(12) United States Patent
Tabak et al.

(10) Patent No.: US 11,776,677 B2
(45) Date of Patent: Oct. 3, 2023

(54) COMPUTER VISION-BASED ANALYSIS OF PROVIDER DATA

(71) Applicant: Pearl Inc., Beverly Hills, CA (US)

(72) Inventors: Joshua Alexander Tabak, Los Angeles, CA (US); Hamza Surti, Los Angeles, CA (US); Ophir Tanz, Los Angeles, CA (US); Cambron Neil Carter, Los Angeles, CA (US)

(73) Assignee: Pearl Inc., West Hollywood, CA (US)

( * ) Notice: Subject to any disclaimer, the term of this patent is extended or adjusted under 35 U.S.C. 154(b) by 0 days.

(21) Appl. No.: 17/569,370

(22) Filed: Jan. 5, 2022

(65) Prior Publication Data
US 2022/0215928 A1    Jul. 7, 2022

Related U.S. Application Data

(60) Provisional application No. 63/233,179, filed on Aug. 13, 2021, provisional application No. 63/134,524, filed on Jan. 6, 2021.

(51) Int. Cl.
*G16H 20/40*    (2018.01)
*G16H 10/60*    (2018.01)

(52) U.S. Cl.
CPC .............. *G16H 20/40* (2018.01); *G16H 10/60* (2018.01)

(58) Field of Classification Search
CPC .................................. G06Q 10/10; A61C 8/00
(Continued)

(56) References Cited

U.S. PATENT DOCUMENTS

| | | | |
|---|---|---|---|
| 5,579,393 | A | 11/1996 | Conner et al. |
| 5,839,438 | A | 11/1998 | Grattinger et al. |

(Continued)

FOREIGN PATENT DOCUMENTS

| | | |
|---|---|---|
| CA | 2275574 | 7/2003 |
| CN | 107 871 285 | 4/2018 |

(Continued)

OTHER PUBLICATIONS

"Detecting periodontal disease using convolutional neural networks", published on IEEE, by Shannah Aberin and Joel Goma, School of information technology, Mapua University, Date of Conference: Nov. 29-Dec. 2, 2018 (IEEE Xplore: Mar. 14, 2019) (Year: 2019).*

(Continued)

*Primary Examiner* — Dilek B Cobanoglu
(74) *Attorney, Agent, or Firm* — Knobbe, Martens, Olson & Bear, LLP

(57) ABSTRACT

Systems and methods are described for utilizing machine learning techniques to analyze data associated with one or more dental practices to identify missed treatment opportunities, future treatment opportunities, or provider performance metrics. The treatment opportunities or performance metrics may be determined or identified based at least in part on a comparison of patient data, such as data stored in association with a dental office's practice management system, with the output of one or more machine learning models' processing of associated radiograph images of the dental office's patients. The one or more machine learning models may include models that identify, from image data of a radiograph, a dental condition depicted in the radiograph, which may be mapped by a computer system to a corresponding dental treatment recommended for the identified dental condition.

15 Claims, 24 Drawing Sheets

(58) Field of Classification Search
USPC .............................................. 705/2; 600/408
See application file for complete search history.

(56) References Cited

U.S. PATENT DOCUMENTS

| | | | |
|---|---|---|---|
| 6,409,504 B1 | 6/2002 | Jones et al. | |
| 6,736,776 B2 | 5/2004 | Miles | |
| 7,269,278 B2 | 9/2007 | Cong et al. | |
| 7,421,398 B2 | 9/2008 | Kimmel | |
| 7,472,275 B2 | 12/2008 | Arnouse | |
| 7,602,965 B2 | 10/2009 | Hong et al. | |
| 7,822,621 B1 | 10/2010 | Chappel | |
| 8,417,010 B1* | 4/2013 | Colby | G06T 7/0012 378/207 |
| 8,463,716 B2 | 6/2013 | Montgomery et al. | |
| 8,687,859 B2 | 4/2014 | Yan et al. | |
| 8,706,517 B2* | 4/2014 | Rowe | G06Q 10/10 705/2 |
| 8,761,493 B2 | 6/2014 | Chen et al. | |
| 8,768,016 B2 | 7/2014 | Pan et al. | |
| 8,929,635 B2 | 1/2015 | Chen et al. | |
| 9,020,236 B2 | 4/2015 | Wang et al. | |
| 9,339,245 B2 | 5/2016 | Colby | |
| 9,477,649 B1 | 10/2016 | Davidson et al. | |
| 9,839,402 B2 | 12/2017 | Colby | |
| 9,886,178 B2 | 2/2018 | Kendall et al. | |
| 10,043,073 B2 | 8/2018 | Ross et al. | |
| 10,049,457 B2 | 9/2018 | Abraham et al. | |
| 10,201,318 B2 | 2/2019 | Tsuji et al. | |
| 10,410,363 B2 | 9/2019 | Dekel et al. | |
| 10,426,351 B2 | 10/2019 | Abrams et al. | |
| 10,722,191 B2 | 7/2020 | Colby | |
| 10,818,386 B2 | 10/2020 | Yao et al. | |
| 10,869,608 B2 | 12/2020 | Dormer et al. | |
| 10,902,940 B2 | 1/2021 | Lyman et al. | |
| 10,937,108 B1 | 3/2021 | Tabak et al. | |
| 10,984,529 B2 | 4/2021 | Carter et al. | |
| 11,055,789 B1 | 7/2021 | Tabak et al. | |
| 2003/0182117 A1 | 9/2003 | Monchi et al. | |
| 2005/0027172 A1* | 2/2005 | Benavides | G16H 10/20 128/920 |
| 2005/0203777 A1 | 9/2005 | Rosenfeld et al. | |
| 2006/0147872 A1 | 7/2006 | Andreiko | |
| 2006/0173985 A1 | 8/2006 | Moore | |
| 2007/0067185 A1 | 3/2007 | Halsted et al. | |
| 2007/0217648 A1 | 9/2007 | Muehlbauer | |
| 2007/0271226 A1 | 11/2007 | Zhang et al. | |
| 2007/0294104 A1 | 12/2007 | Boaz et al. | |
| 2009/0076960 A2 | 3/2009 | Hamel et al. | |
| 2011/0119088 A1 | 5/2011 | Gunn | |
| 2011/0153351 A1 | 6/2011 | Vesper et al. | |
| 2011/0176712 A1 | 7/2011 | Hill et al. | |
| 2012/0076422 A1 | 3/2012 | Yang et al. | |
| 2012/0148986 A1 | 6/2012 | Yan et al. | |
| 2012/0230560 A1 | 9/2012 | Spitz et al. | |
| 2013/0022251 A1 | 1/2013 | Chen et al. | |
| 2013/0185331 A1 | 7/2013 | Conemac | |
| 2014/0142984 A1 | 5/2014 | Wright et al. | |
| 2014/0149128 A1 | 5/2014 | Getchius | |
| 2014/0278529 A1 | 9/2014 | Matos | |
| 2014/0314288 A1 | 10/2014 | Roychowdhury et al. | |
| 2014/0355880 A1 | 12/2014 | Xuan et al. | |
| 2014/0379361 A1 | 12/2014 | Mahadkar et al. | |
| 2015/0046181 A1 | 2/2015 | Adjaoute | |
| 2015/0237106 A1 | 8/2015 | Golay | |
| 2016/0014288 A1 | 1/2016 | Ono | |
| 2016/0038092 A1* | 2/2016 | Golay | A61C 8/00 600/408 |
| 2016/0081620 A1 | 3/2016 | Narayanan et al. | |
| 2016/0196389 A1 | 7/2016 | Moturu et al. | |
| 2016/0220200 A1 | 8/2016 | Sandholm et al. | |
| 2016/0267226 A1 | 9/2016 | Xu et al. | |
| 2017/0053562 A1 | 2/2017 | Bova et al. | |
| 2017/0083672 A1 | 3/2017 | Juneau et al. | |
| 2017/0161439 A1 | 6/2017 | Raduchel et al. | |
| 2018/0122509 A1 | 5/2018 | Christiansson | |
| 2018/0174367 A1 | 6/2018 | Marom | |
| 2018/0206940 A1 | 7/2018 | Kopelan et al. | |
| 2018/0235437 A1 | 8/2018 | Ozerov et al. | |
| 2018/0325484 A1* | 11/2018 | Patel | G16H 30/20 |
| 2018/0366225 A1 | 12/2018 | Mansi et al. | |
| 2019/0066835 A1 | 2/2019 | Lyman et al. | |
| 2019/0110753 A1 | 4/2019 | Zhang et al. | |
| 2019/0130566 A1 | 5/2019 | Niemeijmer et al. | |
| 2019/0236614 A1 | 8/2019 | Burgin et al. | |
| 2019/0313963 A1* | 10/2019 | Hillen | G06N 3/0454 |
| 2020/0012884 A1 | 1/2020 | Zhao et al. | |
| 2020/0100724 A1* | 4/2020 | Golay | G16H 70/60 |
| 2020/0134823 A1 | 4/2020 | Emoto et al. | |
| 2020/0138518 A1 | 5/2020 | Lang | |
| 2020/0146646 A1 | 5/2020 | Tuzoff | |
| 2020/0305808 A1 | 10/2020 | Ezhov et al. | |
| 2020/0381105 A1 | 12/2020 | Bernard et al. | |
| 2021/0012426 A1 | 1/2021 | Brooks et al. | |
| 2021/0073977 A1 | 3/2021 | Carter et al. | |
| 2021/0074425 A1 | 3/2021 | Carter et al. | |
| 2021/0224919 A1 | 7/2021 | Tabak et al. | |
| 2021/0327000 A1 | 10/2021 | Tabak et al. | |
| 2021/0353393 A1* | 11/2021 | Kearney | G06N 3/088 |
| 2021/0383480 A1 | 12/2021 | Tabak et al. | |

FOREIGN PATENT DOCUMENTS

| | | |
|---|---|---|
| CN | 208172859 | 11/2018 |
| CN | 109658260 A | 4/2019 |
| EP | 3407229 A1 | 11/2018 |
| EP | 3503 038 | 6/2019 |
| JP | 2005050246 A1 | 2/2005 |
| KR | 2005020139 A | 3/2005 |
| WO | WO2003071380 A2 | 8/2003 |
| WO | WO2018022705 A1 | 2/2018 |
| WO | WO2021046241 | 3/2021 |
| WO | WO2021146452 | 7/2021 |
| WO | WO2022150821 | 7/2022 |

OTHER PUBLICATIONS

Deep Learning for the Radiographic Detection of Periodontal Bone Loss, Joachim Krois, www.nature.com/scientificreports, Jun. 11, 2019 (Year: 2019).*
Fracaro et al., "The Sensitivity and specificity of Clinical Assessment Compared with Bitewing Radiology for Detection of Occlusal Dentin Caries", American Academy of Pediatric Dentistry 23:3. Mar. 22, 2001 ,204-210.
Markowitz et al. "In Vitro Study of the Diagnostic Performance of the Spectra Caries Detention Aid", The Journal of Clinical Dentistry, 2015,17-22,vol. XXXVI No. 1.
Lee et al. "Diagnosis and Prediction of Periodontally Compromised Teeth Using a Deep Learning-Based Convolutional Neural Network Algorithm", Journal of Periodontal & Implant Science, Apr. 23, 2018,114-123,Apr 48(2).
Lee et al., "Detection and Diagnosis of Dental Caries Using Deep Learning-Based Convolutional Neural Network Algorithm", Journal of Dentistry, Jul. 25, 2018, 106-111, 77.
Hwang et al. "An Overview of Deep Learning in the Field of Dentistry", Image Science in Dentistry, Mar. 25, 2019, 1-7,49.
Murata et al.,"Towards a Fully Automated Diagnostic System for Orthodontic Treatment in Dentistry," IEEE Computer Society, 2017, 1-8, 13th international conference on eScience.
Ahmed, Musheer, "Augmenting Accountability, Security and Fraud Detection in Health Data Sharing Systems", Georgia Institute of Technology, May 2016.
"8 Rules for E-Signature Security", SIGNiX, 2014.
Reducing Healthcare Fraud in Africa; Genkey Solutions b.v., 2016.
McCormick, John, "AI Helps Spot Dental Fraud", Wall Street Journal, Jan. 24, 2020, available at https://www.wsj.com/articles/ai-helps-spot-dental-fraud-11579861801.
Shankeeth et al., "Automated detection of third molars and mandibular nerve by deep learning" (pp 1-7), Jun 21, 2019.

(56) References Cited

OTHER PUBLICATIONS

S. B. Kotsiantis, "Supervised Machine Learning: A Review of Classification Techniques", Jul. 16, 2007, Informatica 31 (2007) 249-268.
L. C. Rabelo, A. Jones and Y. Yih, "Development of a real-time learning scheduler using reinforcement learning concepts," 1994.
R. Ho, "Pragmatic Programming Techniques: Characteristics of Machine Learning Model", Feb. 19, 2012, BlogSpot, all pages.
Azmi et al., "Freeman Chain Code Representation in Signature Fraud Detection Based on Nearest Neighbor and ANN Classifiers", 2014.
Calberson et al., "Fraudulent Use of Digital Radiography: Methods to Detect and Protect Digital Radiographs", 2008, JOE, 34(5).
Young-Jun Yu: "Machine Learning for Dental Image Analysis", Nov. 29, 2016, XP055430578, Retrieved from https://arxiv.org/ftp/arxiv/papers/1611/1611.09958.pdf.
Tian Sukun et al: "Automatic Classification and Segmentation of Teeth on 3D Dental Model Using Hierarchical Deep Learning Networks", IEEE Access, vol. 7, Jul. 15, 2019. pp. 84817-84828, XP011734278, DOI:10.1109/ACCESS.2019.2924262 [retrieved on Jul. 9, 2019].
Arun Anoop M: 11 Image forgery and its detection: A survey, 2015 International Conference on Innovations in Information, Embedded and Communication Systems (ICIIECS), IEEE,Mar. 19, 2015 (Mar. 19, 2015), pp. 1-9 , XP033192551,DOI: 10.1109/ICIIECS.2015.7193253 p. 1-p. 5.
International Search Report and Written Opinion for Application No. PCT/US2021/013475, dated Mar. 15, 2021.
International Search Report and Written Opinion for Application No. PCT/US2020/049237, dated Feb. 8, 2021.
International Search Report and Written Opinion for Application No. PCT/US2022/070051, dated Apr. 21, 2022.

* cited by examiner

Patient Details

[Root Canal ⊗] [+11 ∨]  [📅 2020]  [Brentwood ⊗] [+3 ∨]  [Patient ID]  [Order by Office] [Order by Patient ID] [Order by Severity]  [↓ Download All]

Displaying 30 of 1588 total

| Office | Patient | Bone Loss | Bridge | Calculus | Caries | Crown - metal (including zirconia) | Crown - non-metal | Filling - metal | Filling - non-metal | Implant | Margin Discrepancy | Periapical radiolucency | Root Canal |
|---|---|---|---|---|---|---|---|---|---|---|---|---|---|
| ☐ Brentwood | 4401 | ○ | ○ | ○ | ○ | ◉ | ○ | ○ | ◉ | ○ | ○ | ○ | ○ |
| ☐ Brentwood | 6488 | ◉ | ◉ | ◉ | ○ | ○ | ○ | ◉ | ◉ | ◉ | ◉ | ◉ | ○ |
| ☐ Brentwood | 6888 | ◉ | ◉ | ◉ | ○ | ○ | ○ | ○ | ◉ | ○ | ◉ | ◉ | ○ |
| ☐ Brentwood | 8323 | ◉ | ○ | ○ | ◉ | ◉ | ◉ | ○ | ◉ | ○ | ◉ | ◉ | ○ |
| ☐ Brentwood | 8493 | ◉ | ◉ | ◉ | ◉ | ◉ | ◉ | ◉ | ◉ | ◉ | ◉ | ◉ | ◉ |
| ☐ Brentwood | 0359 | ◉ | ○ | ◉ | ◉ | ◉ | ◉ | ◉ | ◉ | ○ | ◉ | ◉ | ○ |
| ☐ Brentwood | 0529 | ◉ | ○ | ◉ | ◉ | ◉ | ◉ | ○ | ◉ | ○ | ◉ | ◉ | ○ |
| ☐ Brentwood | 0856 | ◉ | ○ | ◉ | ◉ | ◉ | ◉ | ○ | ◉ | ○ | ◉ | ◉ | ○ |
| ☐ Brentwood | 0934 | ◉ | ○ | ◉ | ◉ | ○ | ○ | ○ | ○ | ◉ | ◉ | ◉ | ○ |

| Settings | | |
|---|---|---|
| User Preferences | Office Lists | |
| Group | Offices | Actions |
| Test Group #1 | [Culver ×] [Brentwood ×] [Palms ×] [Weho ×] |  |
| Test Group 2 | [Culver ×] [Palms ×] [Add +] |  |
| [New Group] | | |
FIG. 11

Patients with predicted opportunity for scaling

| | Patient | Office | AI Date | Perio | Endo | Scaling | Implant | Restoration | Restoration Repl... |
|---|---|---|---|---|---|---|---|---|---|
| ☐ | Meda Hood | Brentwood | 03/04/2020 | | Unscheduled | Unscheduled | Predicted | Unscheduled | Unscheduled |
| ☐ | Li Mullen | Culver | 12/12/2019 | | | Predicted | Predicted | Predicted | |
| ☐ | Christena Mcknight | Brentwood | 05/20/2020 | | Unscheduled | Unscheduled | | Unscheduled | Unscheduled |
| ☐ | Shallan Davar | Palms | 06/01/2020 | | Predicted | Predicted | Predicted | Predicted | Predicted |
| ☐ | Amberly Buckley | Culver | 06/04/2019 | Predicted | Predicted | Predicted | Predicted | Predicted | Predicted |
| ☐ | Nestor Serrano | Brentwood | 02/20/2020 | | Unscheduled | Predicted | Predicted | Unscheduled | Predicted |

Displaying 38 entries

FIG. 14

More Filters

— Conditions/Restorations Found by AI
- ☐ Bone Loss  ☐ Bridge
- ☐ Calculus  ☐ Caries
- ☐ Crown  ☐ Edentulous
- ☐ Filling  ☐ Implant
- ☐ Margin Discrepancy  ☐ Periapical radiolucency
- ☐ Root Canal  ☐ Widened PDL — AI detection Date
< April 2021     May2021 >

Save

Robb's Tratments

| Assessment | Status | Actions | Opportunity | Relevant AI Detections |
|---|---|---|---|---|
| Filling | Predicted | Plan | $1,500 | ○ Carries, Margin, Discrepancy |
| Deep Cleaning | Planned | Change | $700 | Bone Loss |
| Implant Opportunity | Outstanding | Reschedule ⊠ | $3,500 | Hopeless Tooth |

Plus Add New Treatment

Perio   0mm  10🦷  3mm  10🦷  6mm+ 12🦷      ⤴ Gradually Worsening ⌵

⤴ Worsening

⤑ Gradually Worsening

→ No Change

FIG. 22

COMPUTER VISION-BASED ANALYSIS OF PROVIDER DATA

PRIORITY AND INCORPORATION BY REFERENCE

This application claims benefit of U.S. Provisional Patent Application No. 63/134,524, filed Jan. 6, 2021, and U.S. Provisional Patent Application No. 63/233,179, filed Aug. 13, 2021, which are hereby incorporated by reference in their entirety.

Any and all applications for which a foreign or domestic priority claim is identified in the Application Data Sheet as filed with the present application are hereby incorporated by reference under 37 CFR 1.57.

BACKGROUND

In the fields of dentistry and other medical disciplines, flawed or inconsistent readings of X-ray images and other medical radiographs are relatively common, as are inaccurate diagnoses made from visual observation of a patient in the absence of a radiograph. For example, in the field of dentistry, a patient's teeth and/or an X-ray of a patient's teeth may be examined by a dentist for diagnosis or other purposes using the dentist's own judgment informed by experience and training. An individual dentist, doctor or other health provider may have limited experience with a particular diagnosis, anatomy or anomaly, which may lead to inaccurate or missed diagnoses or treatment recommendations. Furthermore, two health providers may have different opinions with respect to a diagnosis or treatment plan based on review of the same radiograph or set of radiographs captured for a particular patient. In the field of dentistry, dental practices often utilize existing computer software to manage various aspects of their practice. For example, existing practice management software or systems may include features such as patient scheduling, charting, radiograph image review, and/or other features.

BRIEF DESCRIPTION OF THE DRAWINGS

The foregoing aspects and many of the attendant advantages will become more readily appreciated as the same become better understood by reference to the following detailed description, when taken in conjunction with the accompanying drawings, wherein:

FIGS. 4A, 4B, 5A, 5B, 6 and 7 depict illustrative user interfaces that present information generated based on automated analysis of radiographs and patient records, according to some embodiments.

FIG. 11 depicts an illustrative user interface that enables a user to define settings that include grouping offices or practices.

FIG. 14 depicts an illustrative user interface that presents a visual or graphical representation of the amount of patient treatment opportunities in different categories as determined using machine learning.

FIG. 15 depicts an illustrative user interface that provides options to a user for filtering patient information such as that shown in FIG. 14.

FIG. 16 depicts an illustrative user interface providing an overview of a schedule for a given day for a dental office or dental practice.

FIGS. 21 and 22, which may each be accessible from or part of the user interface of FIG. 20, provide an overview of treatments for the patient (predicted, planned and outstanding), as well as perio chart or pocket/probe depth information for each of the patient's teeth as determined via machine learning.

DETAILED DESCRIPTION

Efficiently managing dental practices with hundreds or even thousands of patients can be difficult without highly specialized data from which staff can make sound decisions. For example, determining the answers to various practice management and performance questions, such as how well a dental practice's new graduate doctors are diagnosing accurate treatments compared to that practice's most seasoned and experienced dentists, is a cumbersome and imprecise process using typical existing systems. Another sample problem that may be difficult to assess using existing systems, for example, is whether a practice has enough patients consulting on a particular issue (such as their wisdom teeth) to bring in a specialist to the office at a certain frequency (such as twice per week). In answering these and many other questions, a practice may rely on approaches that could include a manual review on a case-by-case sampling of patient data, as well as subjective opinions of a reviewing practitioner. Decisions such as these can influence everything from hiring and firing to marketing, training, and return on investment.

Generally described, aspects of the present disclosure relate to computer-implemented processes and system architectures for utilizing computer vision and associated machine learning techniques to drill down to the office-specific data that matters to various stakeholders, and presents actionable information via user interfaces that will be described herein. In some embodiments, the machine learning approaches to analyzing various dental practices' data sets discussed herein may include utilizing computer vision techniques to identify any of various pathologies, conditions, anatomies, anomalies or other medical issues depicted in a radiograph image, such as using systems and methods disclosed in U.S. patent application Ser. No. 16/562,286, entitled SYSTEMS AND METHODS FOR AUTOMATED MEDICAL IMAGE ANALYSIS, filed Sep. 5, 2019 (hereinafter "the '286 application"), the entirety of which is hereby incorporated by reference herein. In some embodiments, treatment opportunities and/or provider performance metrics may be determined or identified based at least in part on a comparison of patient data stored in a dental office's practice management system ("PMS") with the output of machine learning models' processing of associated radiograph image(s), such as according to models disclosed in the '286 application.

Figure 1:
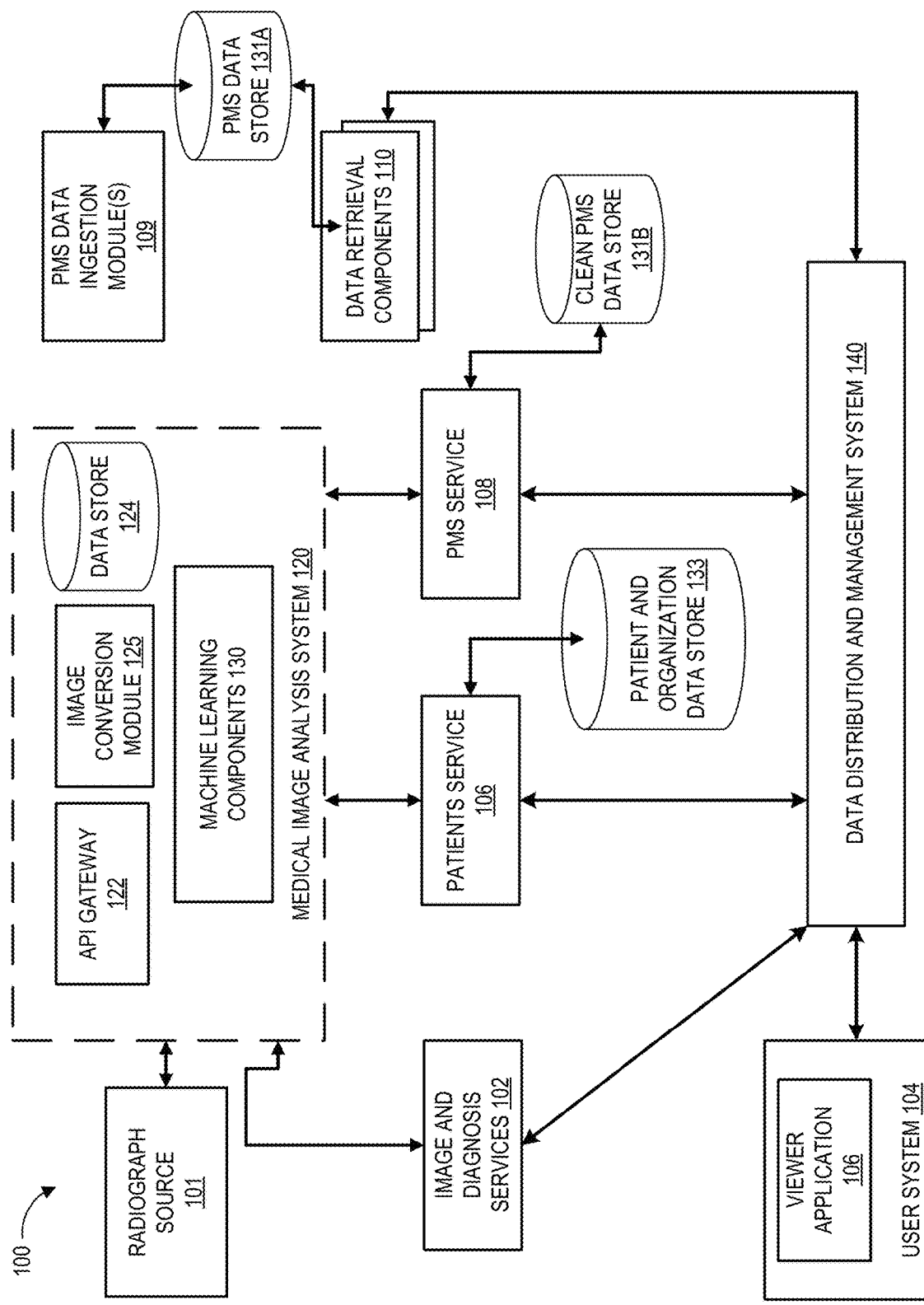
FIG. 1 illustrates a networked computing environment suitable for implementing features for assessing missed opportunities and performance for one or more medical office locations or practices, according to some embodiments.

FIG. 1 illustrates a networked computing environment 100 suitable for implementing features of the present disclosure, according to some embodiments. The environment 100 includes a radiograph source 101, image and diagnosis services 102, user system 104, medical image analysis system 120, patients service 106, PMS service 108, patient and organization data store 133, PMS data store 131A, clean PMS data store 131B, PMS data ingestion module(s) 109, data retrieval components 110, and data distribution and management system 140. Individual components, systems or services illustrated in FIG. 1 may communicate with one another using a network (not illustrated), such as the Internet. Individual ones of the illustrated components, systems or services may communicate via multiple distinct and/or distributed networks as one another, via a single network, and/or may be local to one another.

The user system 104 may be operated by a user associated with a dental practice, provider network, Dental Support Organization ("DSO") that provides business management and support for dental offices, and/or other stakeholder in managing one or more practices. Such a user may be responsible for directing or managing one or more doctors or dentists, such as managing non-clinical aspects of the doctor's or dentist's practice. In some embodiments, the viewer application 106 may be installed on one or more computer systems operated by a DSO, where the viewer application may present user interfaces such as those that will be described with respect to FIGS. 4A, 4B, 5A, 5B, 6, 7 and 9-11 below.

The medical image analysis system 120 can include API gateway 122, one or more data stores 124, an image conversion module 125, and machine learning components 130. The machine learning components may include multiple pre-processing classifiers, machine learning models, and post-processors, such as those further discussed in the '286 application. As will be discussed below, the API gateway 122 can communicate with the radiograph source 101 and the illustrated services 102, 106 and 108 (e.g., using a network, such as the Internet) to receive various information or files (such as radiograph images, patient data, practice data, etc., as will be further discussed below), and to coordinate subsequent image processing and analysis by the machine learning components 130. The various systems, services and other components illustrated in FIG. 1, including interactions or communications between them, will be described in more detail below with respect to FIGS. 2 and 3.

The PMS data ingestion modules 109 may each be configured to ingest data from a different type of PMS data scheme. For example, different practice management systems or software utilized by individual dental practices include, among others, offerings from Dentrix and Open Dental. These and other software or systems may format data differently from one another. In FIG. 1, a different PMS data ingestion module 109 may be implemented for each data schema or PMS type, and may store the data in one or more PMS data stores 131A. The data retrieval components 110 may retrieve the various formatted data from data store 131A and may be configured to translate, normalize and/or convert the data into a standardized format following a data schema specific to the environment of FIG. 1, which the PMS service 108 and data distribution and management system 140 (among others) may be configured to receive and analyze as appropriate. The clean, normalized PMS data may be stored in clean PMS data store 131B, such as via the data distribution and management system 140 managing communications that include the PMS service 108 receiving data output by the data retrieval components 110, then the PMS service 108 storing the data in data store 131B. The PMS data may include, for example, data regarding various patients and the treatment history from past office visits (such as treatment codes).

The medical image analysis system 120 may analyze radiograph image files from radiograph source 101 and provide clean output of the machine learning models (as will be discussed further below) to the image and diagnosis service 102. This data may include, for example, annotated radiograph images and/or other data indicating conditions, pathologies, anatomies, restorations and/or anomalies identified by the machine learning components 130 in one or more radiograph images.

Patients service 106 may receive the machine learning output from the image and diagnosis service 102 as well as the PMS data for particular patient identifiers from the PMS service 108. The patients service 106 may implement various functionality, which will be described with reference to FIG. 3 and other figures below, including pre-computing various results of comparing the machine learning output and PMS data for specific patient identifiers, which may then be populated into user interfaces. Mapping data associating a patient ID from the radiograph data and a corresponding patient ID from the PMS data may be stored in patient and organization data store 133. The patients service 106 may also access the data store 133 or another data store to identify which conditions or indications map to or should result in particular treatments. The data store 133 may additionally store lists of patients for particular providers of interest to a given user (such as patients seen at particular offices), which the patients service 106 may use to obtain the listed patients' data from both the PMS service and image and diagnosis services.

Each of the various systems and services illustrated in FIG. 1 may include hardware and software components for establishing communications over a communication network. For example, each may be equipped with networking equipment and network software applications that facilitates communications via one or more networks (for example, the Internet, an intranet or a virtual private network). Each of the systems, modules, components or services in FIG. 1 may have or utilize varied local computing resources such as central processing units and architectures, memory, mass storage, graphics processing units, communication network availability and bandwidth, and so forth. Further discussion of various hardware components that may be employed within environment 100 will be further described with respect to FIG. 8 below. The data stores may employ various security and privacy protocols known in the art for storage of medical data, including Health Insurance Portability and Accountability Act ("HIPAA") compliance.

Figure 2:
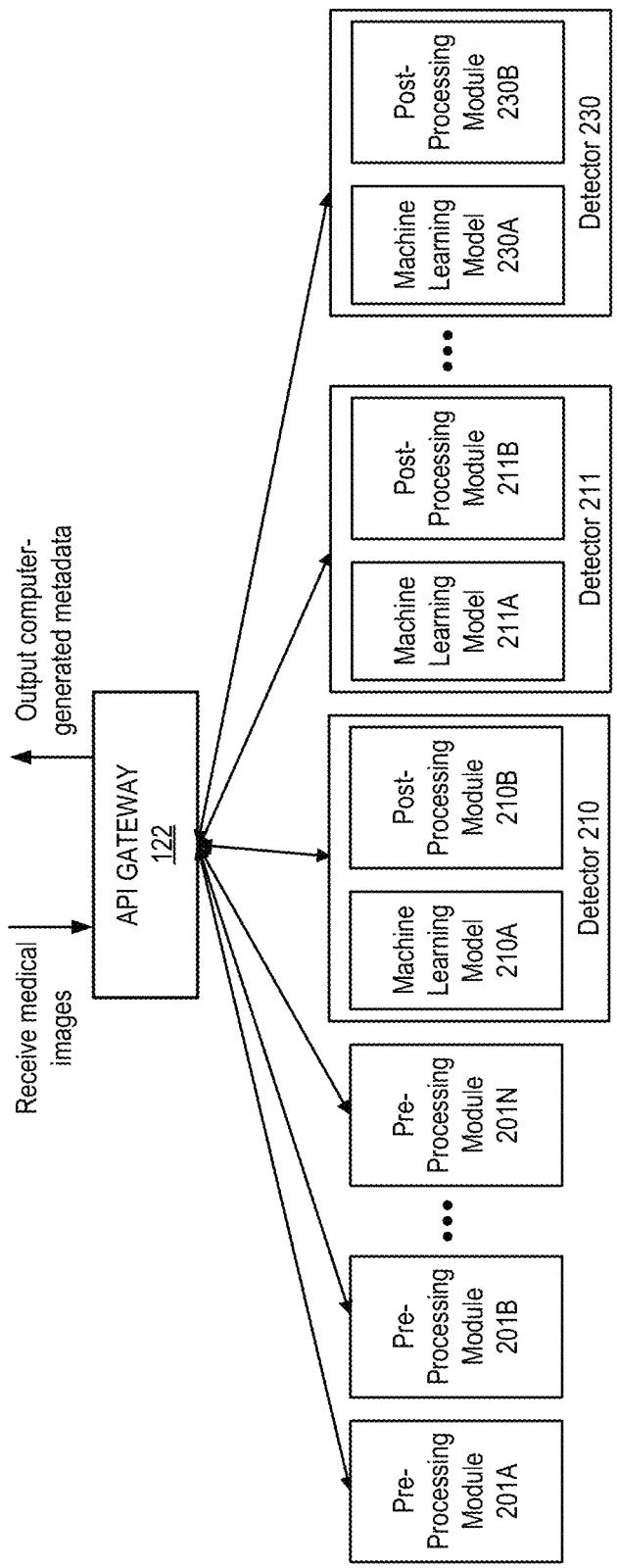
FIG. 2 illustrates a number of different pre-processing modules, machine learning models, and post-processing modules that may be collectively implemented in order to detect different pathologies, anatomies, restorations and/or anomalies depicted in a radiograph.

FIG. 2 illustrates a number of different pre-processing modules, machine learning models, and post-processing modules that may be collectively implemented in order to detect different pathologies, anatomies, restorations and/or anomalies depicted in a radiograph. The API gateway 122 may generally be responsible for managing calls to various routines and models for generating metadata, such as labels or classifications of pathologies, anatomies, restorations, anomalies, etc., along with optional image annotation data (such as bounding boxes around a given detected pathology, anatomy, etc.). As illustrated, the API gateway 122 makes sequential calls to several pre-processing modules which preprocess the image data, which are shown in FIG. 2 as preprocessing modules 201A, 201B through 201N. It will be appreciated that there may be a large number of pre-processing modules not illustrated.

At least some of the pre-processing modules may generally adjust certain global features in X-rays or other radiograph images by way of image processing. These routines may be configured to enhance and/or standardize the image data before it is processed by machine learning models. One such example of pre-processing is histogram equalization. In some embodiments, the pre-processing modules may include, but are not limited to: (a) a module configured to determine if an image is "whitewashed" such that no image processing techniques (e.g. gamma correction) will sufficiently recover useful information for subsequent processing; (b) a module configured to detect the orientation of the image and adjust the orientation such that subsequent models or modules are only required to handle one orientation; (c) a machine learning model configured to detect teeth or another specific anatomical feature; and/or (d) a machine learning model configured to classify the type of image, such as from possible classifications of panoramic, bitewing, periapical, and/or others. In some embodiments, a pre-processing module may remove or redact personally identifiable information (such as name or patient information) from within images, while in other embodiments the personal information may remain in an image for purposes of image feature input to the machine learning models, with advance approval from the associated parties (but may then be removed or redacted before image display to any user).

After the pre-processing modules have processed a given image, the API gateway 122 makes parallel calls to a number of different machine learning models (such as machine learning models 210A, 211A, 230A, among others) that have been previously trained to localize and classify (or detect) specific pathologies, anatomies, restorations, and/or anomalies. In doing so, the API gateway may pass forward partial metadata generated from the preprocessing modules, such as preprocessing modules 201A, 201B and 201N. This metadata may then be used by the post-processing routines associated with specific machine learning models, such as post-processing modules 210B, 211B and 230B. As illustrated, each detector 210, 211, 230 and others not illustrated may include both a machine learning model and an associated post-processing module that is specific to the given machine learning model, according to some embodiments.

In some embodiments, each of the specific detectors and/or the associated machine learning model may include one of the following, though others may be implemented or some excluded in other embodiments: a model for detecting the presence of bone loss; a model for detecting the presence of faulty restorations (such as restorations which contain open margins, sub margins, or overhangs); a model for detecting caries; a model for detecting recurrent decay; a model for detecting widened periodontal ligaments; a model for detecting existing restorations (such as crowns, root canals, metal and non-metal fillings, bridges, or implants); a model for detecting potential pathologies (such as cysts, bone lesions, cancerous growths or malignancies); a model to detect calculus; a model to detect existing anatomy (such as sinuses, nerves, nasal canals, orbits, or zygomas); a model to detect teeth by number; a model to detect crowns and roots of teeth; a model to detect the size of the airway; a model to detect quantity and quality of dental implant site; a model to detect third molar impaction; a model to detect jaw fractures; a model to detect facial trauma; a model to detect arch forms of jaws; and/or a model to detect orthodontic cephalometric tracings. In some embodiments, a single model may be trained to identify a large set of the above or all of the above, in addition to individual models that detect individual conditions above.

In some embodiments, both a first model and a second model may each individually be configured to detect multiple pathologies that are the same between the two models, but the models may have been trained using different machine learning algorithms. For example, two models employing different machine learning algorithms may each be trained to classify image data as depicting any of the same list of pathologies (such as twenty different pathologies), but may output different classification results for the same input images based on differences in the respective models' training data and/or specific machine learning algorithm or structure used for the particular model. In such embodiments in which two or more machine learning models may be trained to detect the same or overlapping sets of potential pathologies, the system 120 may be configured to apply a voting methodology or other resolution process to determine an ultimate classification result based on collective output of the models. It will be appreciated that many known methods of ensemble learning may be used in embodiments in which multiple alternative models are trained to make similar classification predictions using different supervised and/or unsupervised machine learning techniques. As discussed above, other models may be specific to individual pathologies (such as a model trained to detect only a single pathology as opposed to any of a set of pathology classes or labels).

As discussed further in the '286 application, training of the various machine learning models may include data collection by way of individual annotation and/or consensus-based annotation. Consensus may be arrived at programmatically in some embodiments, such as based on a Jaccard index being determined to be at or above a given threshold between two individual annotations. Consensus annotation may additionally or alternatively come from annotators directly working together to jointly annotate radiographs together. Once the data has reached an acceptable volume and variance (such as with respect to pre-defined feature spaces) it may be used to train the models and may additionally be used for measuring accuracy of the trained models.

The machine learning architectures used for training may include various forms of neural networks, deep learning models, and/or other architectures for accomplishing classification and/or localization via supervised and/or unsupervised learning. In some embodiments, the specific architectures may be selected to achieve two goals: (1) to localize regions in a radiograph which contain features of interest and (2) to classify each of said regions. The final output in most instances will be some number of predicted regions along with associated probabilities of said regions containing a particular pathology, restoration, anatomy, or anomaly of interest. As non-limiting examples according to some embodiments, one or more of the models may resemble or include single shot detector (SSD), faster region-based convolutional neural networks (Faster R-CNN), "You Only Look Once" (YOLO) real-time object detection, and/or a U-Net convolutional neural network. It will be appreciated that various other existing or future object detection, localization, and/or classification methodologies may be used for individual models, and that different models within a single embodiment may use different training methodologies and/or machine learning architectures.

As shown in FIG. 2, each machine learning model (such as machine learning model 210A) is coupled with a model-specific post-processing module (such as post-processing module 210B). Post-processing modules may merge, edit, and/or augment the produced metadata based on algorithmically combining output from machine learning models. One such example is reducing false positives in anatomical regions in which the predicted property is known never to exist. The functionality implemented by a given post-processing module may vary based on what the associated machine learning model is designed to localize and classify. For example, if machine learning model 211A is configured to classify caries (which can only exist on teeth), the combination of this caries detection model and a tooth detection pre-processing module may be used by the post-processing module 211B to confirm that the machine learning model 211A did not classify a region as caries if the region was not also classified as a tooth in pre-processing.

In some embodiments, certain machine learning models or detectors may produce metadata that is used by a subsequent detector or machine learning model. For example, in one embodiment, detector 211 may be a sub-detector of detector 210. For example, detector 210 may localize a region in the image which has been predicted to contain a specific pathology, anatomy, restoration and/or anomaly. Then, detector 211 may take this metadata as input and restrict its processing to only those regions of interest to it. As a more specific example, detector 210 may predict the presence of caries. Detector 211 may crop only those regions containing caries (as predicted by detector 210), then detector 211 may classify only those regions for the particular type of carie (e.g. into dentin, into enamel, or into pulp). In some embodiments, there may be more than one sub-detector for a given detector. For example, following the example above, there may also be a sub-detector to classify detected carie regions into differing categories, such as gross, mesial, occlusal/incisal, distal, facial, lingual/palatal, incipient, or recurrent. Once all detectors have generated their respective metadata, the API gateway 122 may construct or generate a final output message or metadata set that is passed as the final response to a requester or other system or service, such as the image and diagnosis services 102 or the patients service 106.

Figure 3:
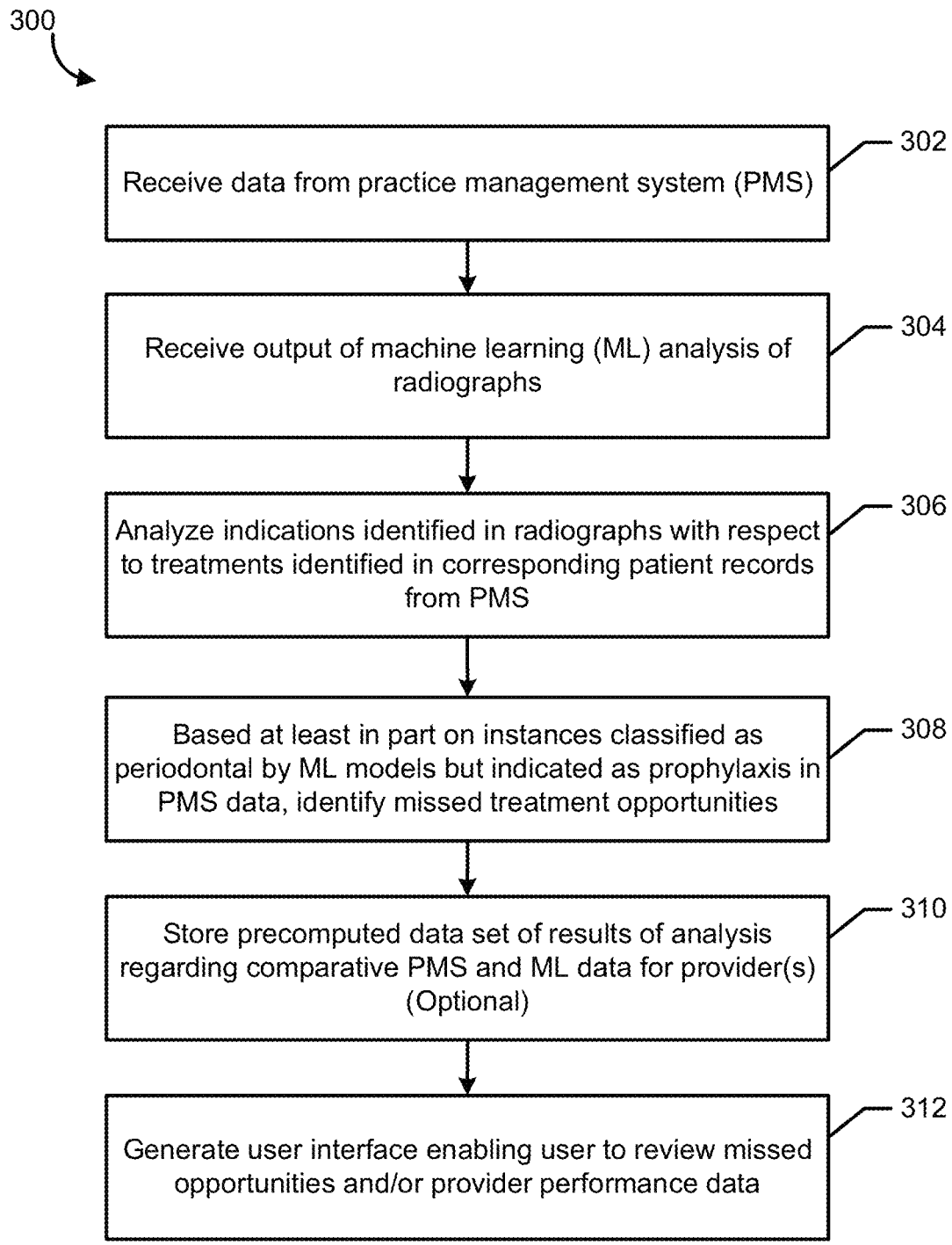
FIG. 3 is a flow diagram of an illustrative method for identifying missed treatment opportunities and presenting associated information in a user interface, according to some embodiments.

FIG. 3 is a flow diagram of an illustrative method 300 for identifying missed treatment opportunities and presenting associated information in a user interface, according to some embodiments. The blocks of illustrative method 300 may each be performed by one or more components illustrated FIG. 1, in some embodiments. For example, in some embodiments, the image and diagnosis services 102, data distribution and management system 140, PMS service 108, and patients service 106 may each perform different aspects of method 300. In other embodiments, a single system may perform the entire method 300, such as patients service 106, based in part on data generated by other illustrated systems or components described above with respect to FIG. 1. For ease of description, the blocks of FIG. 3 will be described below with respect to an embodiment in which they are each performed by the patients service 106, which is not intended to be limiting.

The illustrative method 300 begins at block 302, where the patients service 106 receives PMS data, such as data regarding various patients that recently visited a given dentist's office or other medical practice. The data for a given patient may include, for example, a patient identifier used to identify the patient in an external practice management system or practice management software application, as well as one or more treatment codes identifying treatments or procedures that the dentist or other medical provider provided to the patient during the office visit. The PMS data may also include doctor's notes (such as a note that the doctor saw a given condition and therefore recommended a certain treatment), observations, charts and/or other data stored in a PMS used by the doctor's office. The PMS data may indicate, for a given patient, whether the patient has been classified by the dentist as prophylaxis (prophy) or periodontal (perio). As is known in the art, a prophy appointment may generally refer to a regular cleaning for patients with healthy gums and bone, whereas a perio appointment includes a more involved cleaning in order to control the progression of periodontal disease.

At block 304, the patients service 106 receives output of the machine learning analysis of radiographs associated with the patients for which PMS data was received in block 302. The machine learning output may be received at different times or in a different order from the PMS data for individual patients. As discussed above, the machine learning models' output may be generated by the medical image analysis system 120 in manners described above, then passed to the image and diagnosis services 102, which in turn may provide it to the patients service 106 via the data distribution and management system 140. The patients service 106 may use stored patient identifier mapping data to match the patient identifier stored for a particular radiograph to the same patient's corresponding patient identifier within the PMS data.

At block 306, the patients service 106 analyzes indications identified in radiographs (where a given indication may represent a collection of anatomies, anomalies, and/or conditions detected by the machine learning models from a radiograph image) with respect to treatments identified in corresponding patient records from the PMS data. For example, the patients service 106 may access stored association data that indicates the treatment codes that would typically be entered in PMS data for treating specific conditions or indications, and may identify mismatches where the expected treatment code for a given patient who has a certain indication present in their radiograph does not appear in the patient's corresponding PMS record. Such mismatches may be identified at block 308 as missed treatment opportunities, which may be one or more treatments that a dentist could have or should have performed with respect to a given patient if properly diagnosing the conditions that were identified by the machine learning models from the patient's radiograph(s). These missed opportunities may be identified by the patients service 106 based at least in part on instances of patients classified as perio by the machine learning models (from radiograph image data) but indicated as prophy in the PMS data.

At block 310, the patients service 106 may optionally generate and store (such as in patient and organization data store 133) a precomputed data set of results of the analysis regarding comparative PMS and machine learning data for one or more given providers. For example, in order to more efficiently generate user interfaces later on without querying various components illustrated in operating environment 100, the patients service 106 may periodically update and store a cached set of results that may be later requested by a user. These results may be generated for (and organized by) one or more specific office locations (e.g., only including patients who visit a given physical office location) and/or for a particular user of the system (e.g., for all offices that the user manages). Users may be able to configure or define various parameters and preferences that dictate how the precomputed results will be generated for that user. For example, the user may configure weights applied to different conditions or indications (such as one weight for bone loss and another weight for caries to be used in generating a "hygiene status" score or value), which may be considered to be doctor-specific definitions that will be respected and applied by the system.

At block 312, the patients service 106 or another system or component may generate one or more user interfaces that enables a user to review various information, data and/or metrics discussed herein, such as missed perio opportunities and/or provider performance data. Various illustrative user interfaces will be discussed below. The illustrative method 300 ends after block 312.

FIGS. 4A, 4B, 5A, 5B, 6 and 7 depict illustrative user interfaces that present information generated based on automated analysis of radiographs and patient records, according to some embodiments. In some embodiments, these user interfaces may be generated at least in part by the patients service 106, and may be presented for display by viewer application 106 operating on a user system 104.

Figure 4A:
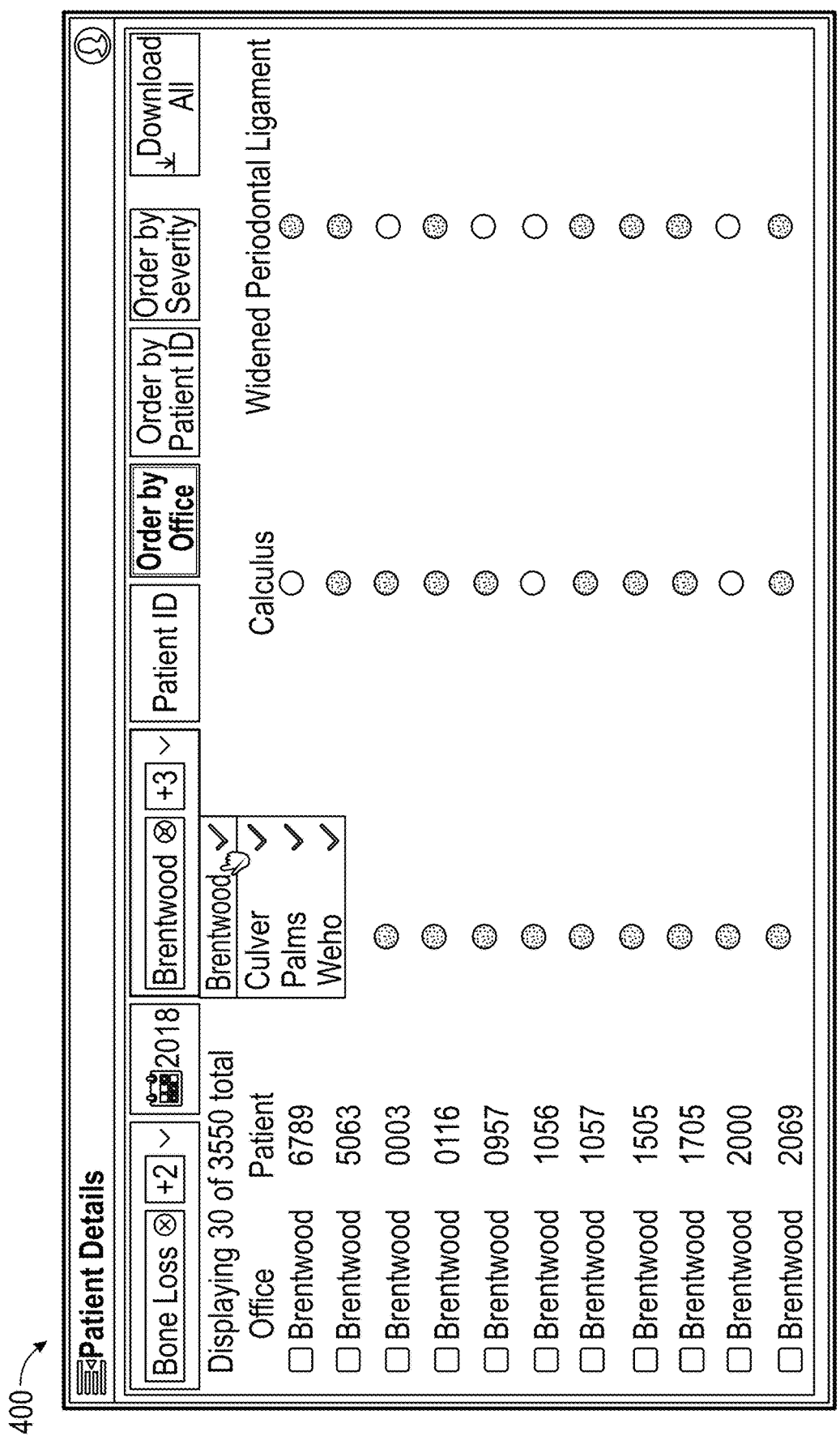

FIG. 4A depicts an illustrative user interface 400 that visually presents information regarding various patients of one or more offices. Each row identifies a specific office and a patient identifier, followed by a series of graphical indicators indicating whether or not a specific indication or condition was present for the patient, which may be determined by the machine learning models described above from radiograph image data. In this example, the empty circular icon in the "Calculus" column for patient #6789 may indicate that the machine learning models did not detect the presence of calculus in the given patient's radiographs, while the solid dark circular icon in the "Widened Periodontal Ligament" column may indicate that the machine learning models did detect the presence of a widened periodontal ligament in the given patient's radiographs. The user may select various sort options for the rows of patient information, such as sorting by office location, by patient identifier, or by severity. Severity may have been determined by the machine learning models, such as based on a score or confidence level that the models output in association with a given classification of the radiograph data. The user may additionally select which office(s) should appear in the list (such as by checking or unchecking office names in the dropdown menu shown in expanded form), may search for a specific patient identifier by entering that identifier as a search string, and may select a time period (e.g., referring to the time period that the radiographs were captured of the patient(s)).

User interface 400 additionally includes options for the user to select which conditions or indications should be included as columns in the display. In user interface 450 of FIG. 4B, the user has selected twelve different columns to be displayed, each corresponding to a different condition or indication selected by the user. The presence or absence of each of these conditions or indications for specific identified patients in the table is shown, as determined from the machine learning models' analysis of radiograph image data. Selecting different filter options may enable the user, for example, to visually identify which patients may be good candidates for particular treatments (such as needing orthodontic treatment) that are appropriate when a given collection or combination of conditions or indications are present for the same patient. A user may use these filters and time period selections to identify potential leads for further treatments over time, and/or may review time periods relevant for a particular appointment time range from the PMS data.

Figure 5A:
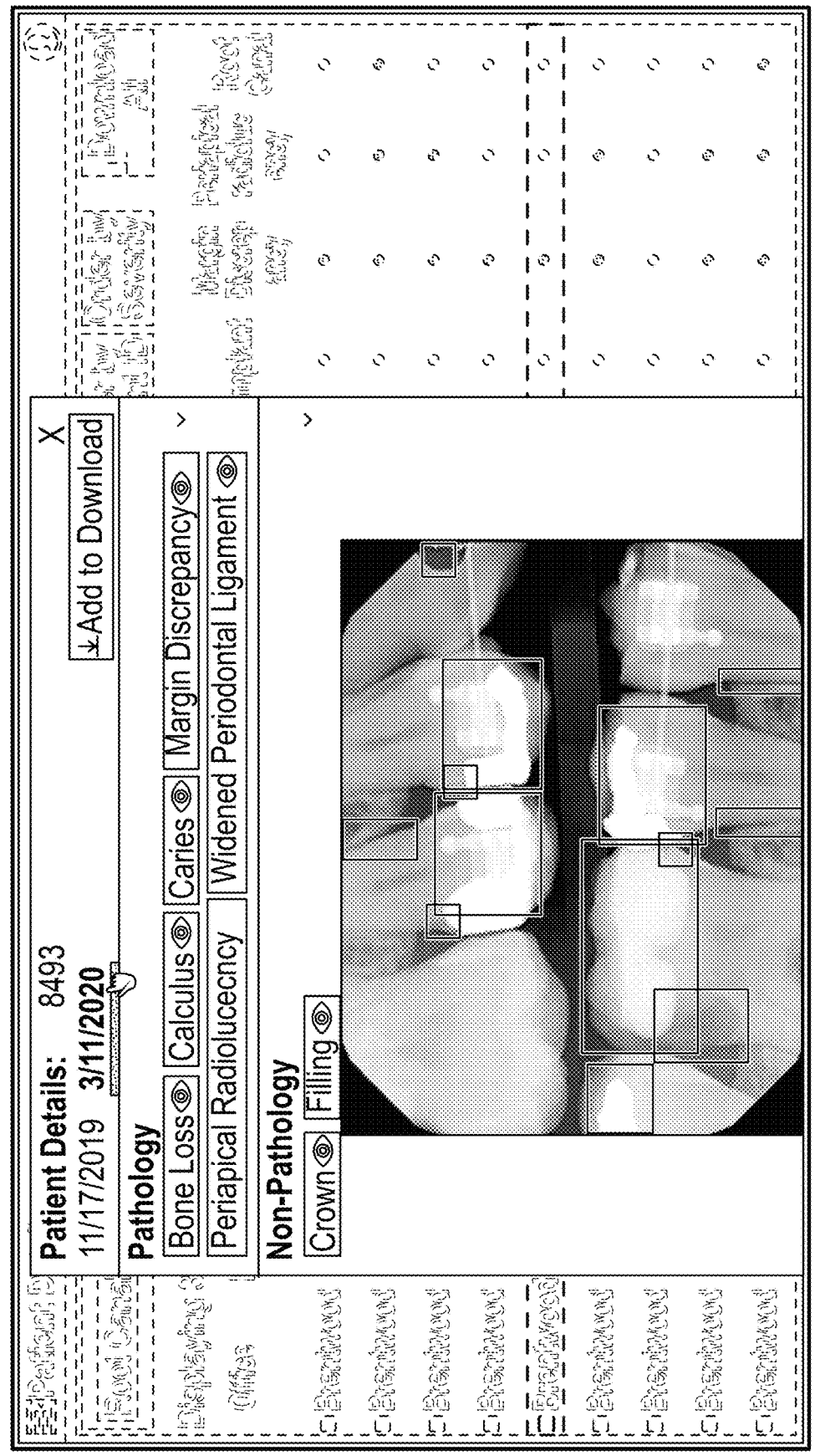
Figure 5B:
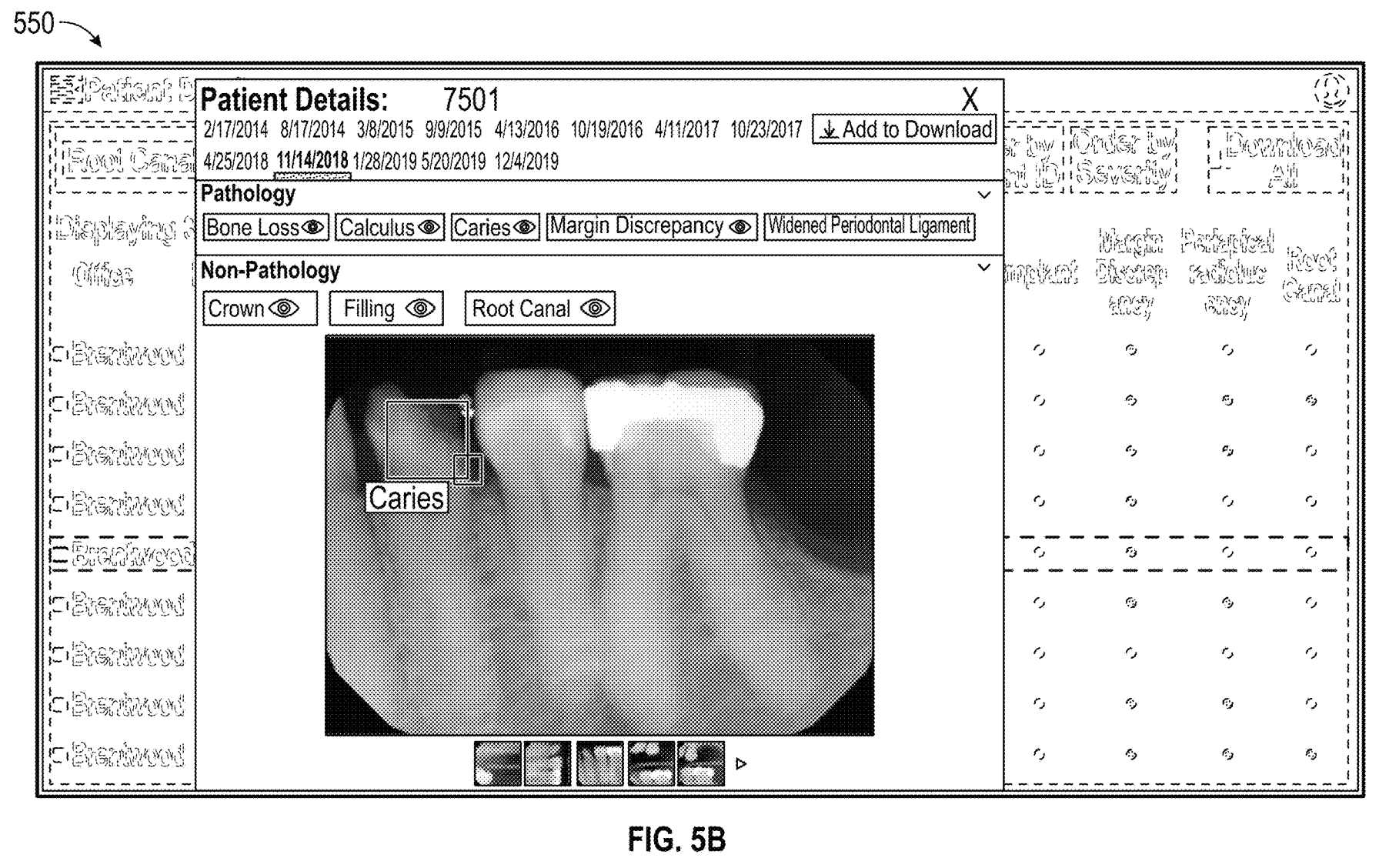

FIGS. 5A and 5B illustrate examples of additional information that may be presented in a user interface in response to a user selecting to view details regarding a specific patient (identified by a patient identifier in user interface 405, for example). In user interface 500, a patient's radiograph image is shown from a particular capture date (Mar. 11, 2020), with bounding boxes shown for various anatomies, anomalies, conditions and/or indications, where the bounding boxes have been determined and added to the radiograph by machine learning models (such as according to methods described above and in the '286 application). The user may select a displayed condition name (such as "bone loss"), which may cause the user interface to update to highlight the bounding box(es) in the radiograph corresponding to that condition. In user interface 550 of FIG. 5B, which may only be presented to users with access privileges or permissions that enable them to modify the radiograph augmentation data, the user is able to remove an indication that the user disagrees with (such as a dentist determining that the output of the machine learning models is incorrect) by selecting the "X" icon on the bounding box marked "caries" in the illustrated example (thereby removing the indication of caries for this patient #7501 for the particular tooth).

Figure 6:
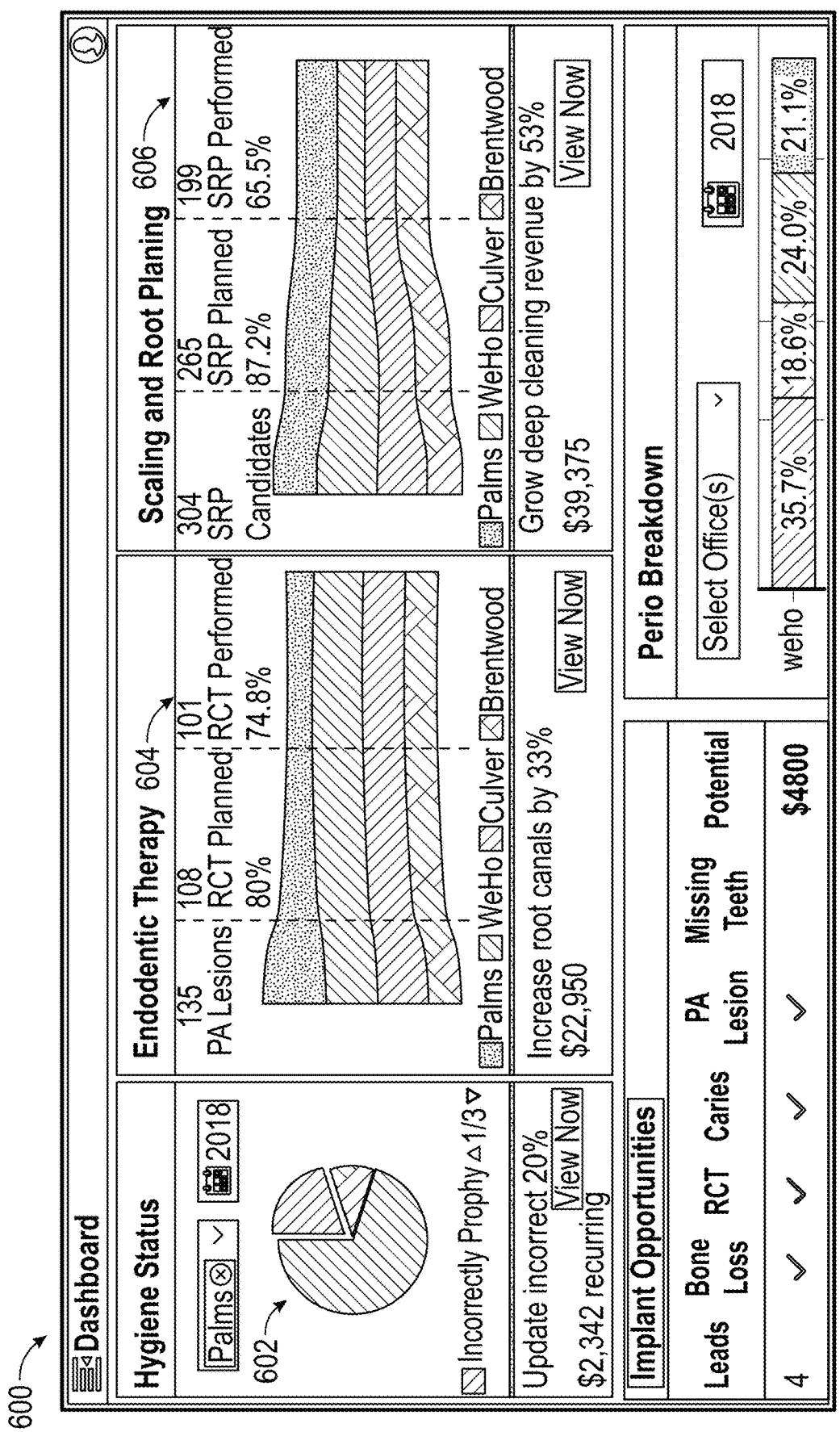
Figure 7:
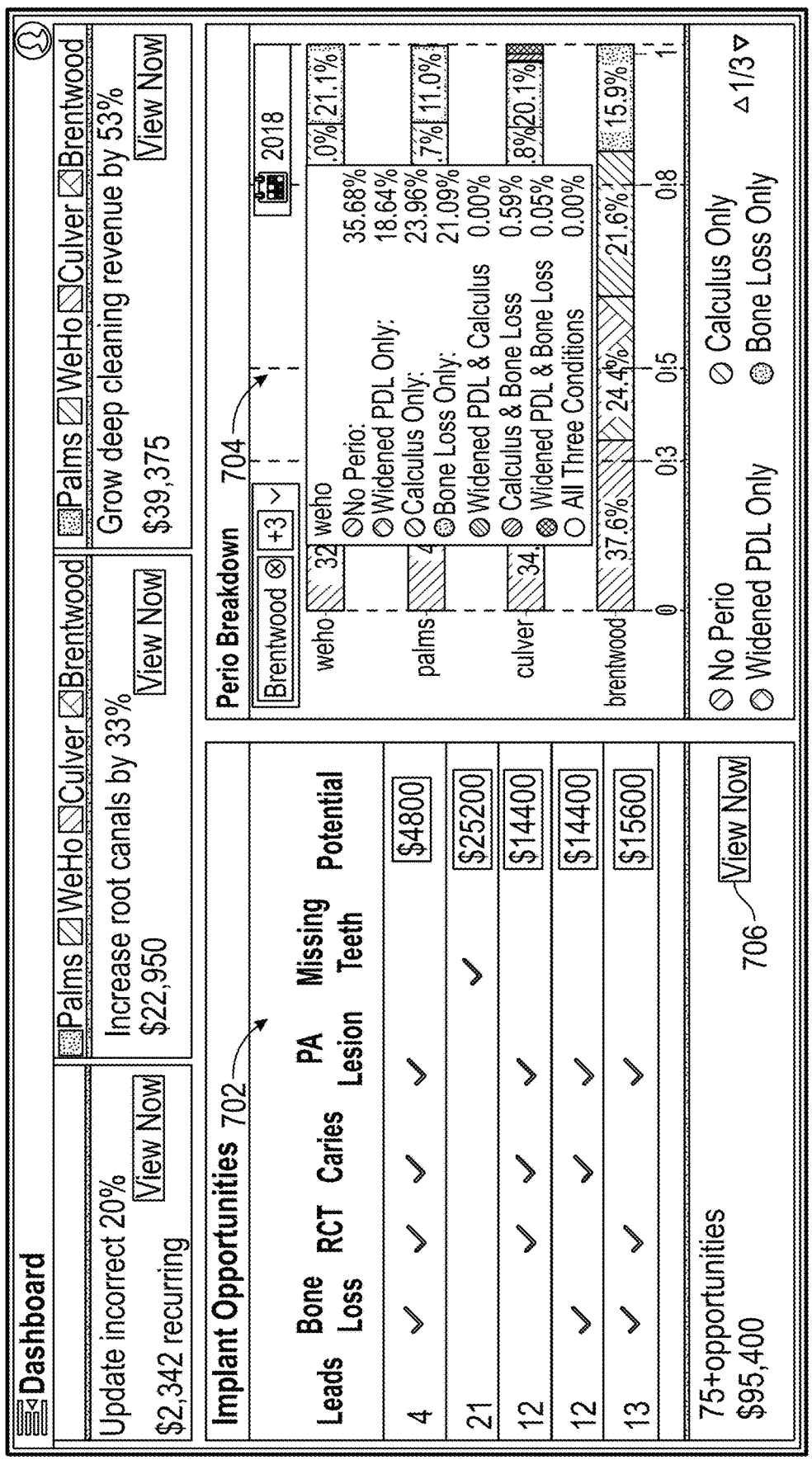

FIGS. 6 and 7 depict illustrative user interfaces 600 and 700 that present various metrics and visualizations generated in the operating environment of FIG. 1, such as by the patients service 106. In some embodiments, user interface 700 may be displayed when a user scrolls down or pages down during display of user interface 600. Depending on the embodiment, features displayed in user interfaces 600 and 700 may be part of the same user interface as each other or may be split into separate user interfaces.

User interface 600 includes a hygiene status graphical display 602 (as a pie chart in the given embodiment) that indicates, for the Palms office in 2018, the relative ratio of "incorrectly prophy" determinations, which may represent the number of percentage of instances within the given office for the given time period that patients were classified as prophy in the PMS data (originally entered by a clinician, for example), but were identified as perio by the machine learning models from analysis of corresponding patient radiographs. These instances may represent patients that are potential leads for further treatment. The display portion 602 additionally indicates that the 20% determined "incorrectly prophy" percentage would lead to $2,342 of recurring revenue if these patients were accurately moved to perio status (e.g., due to increased office visits and/or costs of particular cleaning or other procedures). This revenue amount may be determined from multiplying market averages or office-specific prices per patient per estimated visit frequency, for example.

User interface 600 additionally provides graphical visualizations for both endodontic therapy 604, and for scaling and root planning 606, each comparing the number of instances where the machine learning models identified the relevant indication for a treatment (e.g., 135 instances of PA lesions), the number of corresponding treatments planned to be performed according to the PMS data (108 for root canal therapies planned, which is 80% of theoretical best case if the clinician accurately identified all potential opportunities for root canals identified by the machine learning models), and the number of the corresponding procedure that were actually performed according to the PMS data. The bars are color coded according to the specific office to visually identify how offices are performing relative to each other. The user interface 600 further indicates the corresponding revenue that could be obtained from increasing the number of treatments to cover all opportunities identified by the machine learning models (indicated as a revenue increase of 33% for root canals, and 53% for deep cleaning).

User interface 700 identifies dental implant opportunities 702 and provides a perio breakdown 704 by office location. The period breakdown 702 indicates the number of patient leads identified by the machine learning models for various displayed combinations of conditions, with the corresponding total estimated revenue potential if these leads were acted on by completing the corresponding implant treatments. User selection of the "view now" option 706 may present further information regarding these leads broken down by patient with various filter options (such as those discussed above with respect to FIGS. 4A and 4B). The period breakdown 704 provides color coded bar graphs indicated, for each selected office location, the percentage of patients with various identified indications or conditions, as determined by the output of the machine learning models discussed above. In the example, the user has moused over or selected the "weho" office location to see a detailed listing of percentages and their corresponding legend information.

Figure 8:
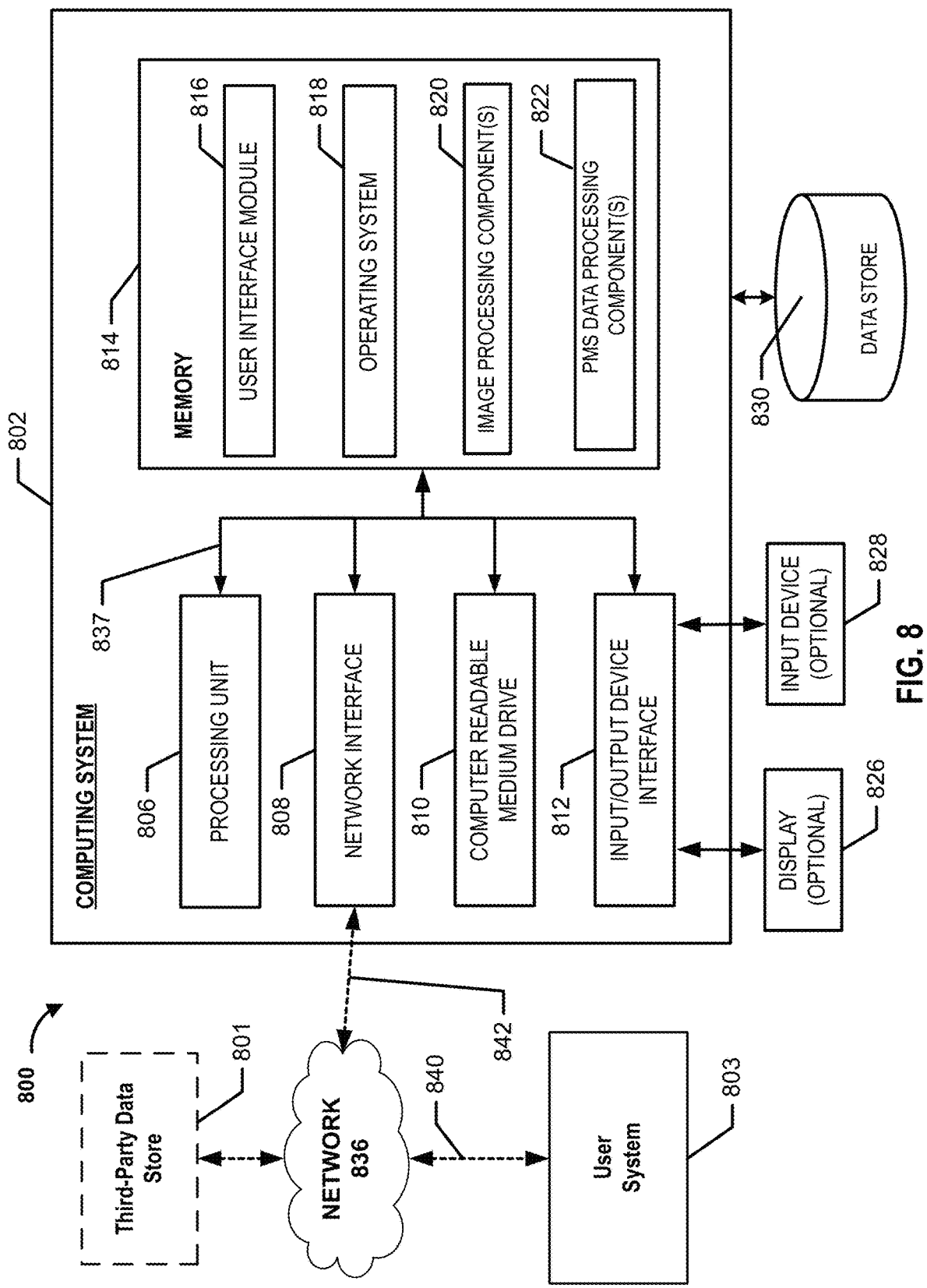
FIG. 8 is a system block diagram of a computing environment suitable for use in various embodiments of the present disclosure.

FIG. 8 illustrates a general architecture of a computing environment 800, according to some embodiments. As depicted in FIG. 8, the computing environment 800 may include a computing system 802. The general architecture of the computing system 802 may include an arrangement of computer hardware and software components used to implement aspects of the present disclosure. The computing system 802 may include many more (or fewer) elements than those shown in FIG. 8. In some embodiments, the computing system 802 may be an example of what is referred to as the patients service 106 above, though other systems and services described above with respect to FIG. 1 may include one or more similar components, in some embodiments. In other embodiments, the computing system 802 may implement functionality of multiple services, systems or components illustrated in FIG. 1, such as the image and diagnosis services 102, the patients service 106 and the PMS service 108.

As illustrated, the computing system 802 includes a processing unit 806, a network interface 808, a computer readable medium drive 810, an input/output device interface 812, an optional display 826, and an optional input device 828, all of which may communicate with one another by way of a communication bus 837. The processing unit 806 may communicate to and from memory 814 and may provide output information for the optional display 826 via the input/output device interface 812. The input/output device interface 812 may also accept input from the optional input device 828, such as a keyboard, mouse, digital pen, microphone, touch screen, gesture recognition system, voice recognition system, or other input device known in the art.

The memory 814 may contain computer program instructions (grouped as modules or components in some embodiments) that the processing unit 806 may execute in order to implement one or more embodiments described herein. The memory 814 may generally include RAM, ROM and/or other persistent, auxiliary or non-transitory computer-readable media. The memory 814 may store an operating system 818 that provides computer program instructions for use by the processing unit 806 in the general administration and operation of the computing system 802. The memory 814 may further include computer program instructions and other information for implementing aspects of the present disclosure. For example, in one embodiment, the memory 814 may include a user interface module 816 that generates user interfaces (and/or instructions therefor) for display upon a computing system, e.g., via a navigation interface such as a browser or application installed on the computing system 802 or the client computing system 803.

In some embodiments, the memory 814 may include one or more image processing components 820 and PMS data processing components 822, which may be executed by the processing unit 806 to perform operations according to various embodiments described herein. The modules 820 and/or 822 may access the data store 830 in order to retrieve and analyze image data and/or PMS data, and to generate other associated data as described herein. Other data stores may also be present in some embodiments. The data store(s) may be part of the computing system 802, remote from the computing system 802, and/or may be a network-based service.

In some embodiments, the network interface 808 may provide connectivity to one or more networks or computing systems, and the processing unit 806 may receive information and instructions from other computing systems or services via one or more networks. In the example illustrated in FIG. 8, the network interface 808 may be in communication with a user system 803 via the network 836, such as the Internet. In particular, the computing system 802 may establish a communication link 842 with a network 836 (e.g., using known protocols) in order to send communications to the computing system 803 over the network 836. Similarly, the computing system 803 may send communications to the computing system 802 over the network 836 via a wired or wireless communication link 840. In some embodiments, the computing system 802 may additionally communicate via the network 836 with an optional third-party data store or data service 801, which may be used by the computing system 802 to retrieve remotely stored image files, patient data, and/or other information, data or files. The computing systems 802 and 803 may be any of a number of computing systems including, but not limited to, a laptop, a personal computer, a mobile phone, a smartphone, a tablet computer, another wireless device, a set-top or other television box, one or more servers, and the like. The system 803 may include similar hardware to that illustrated as being included in computing system 802, such as a display, processing unit, network interface, memory, operating system, etc.

Figure 9:
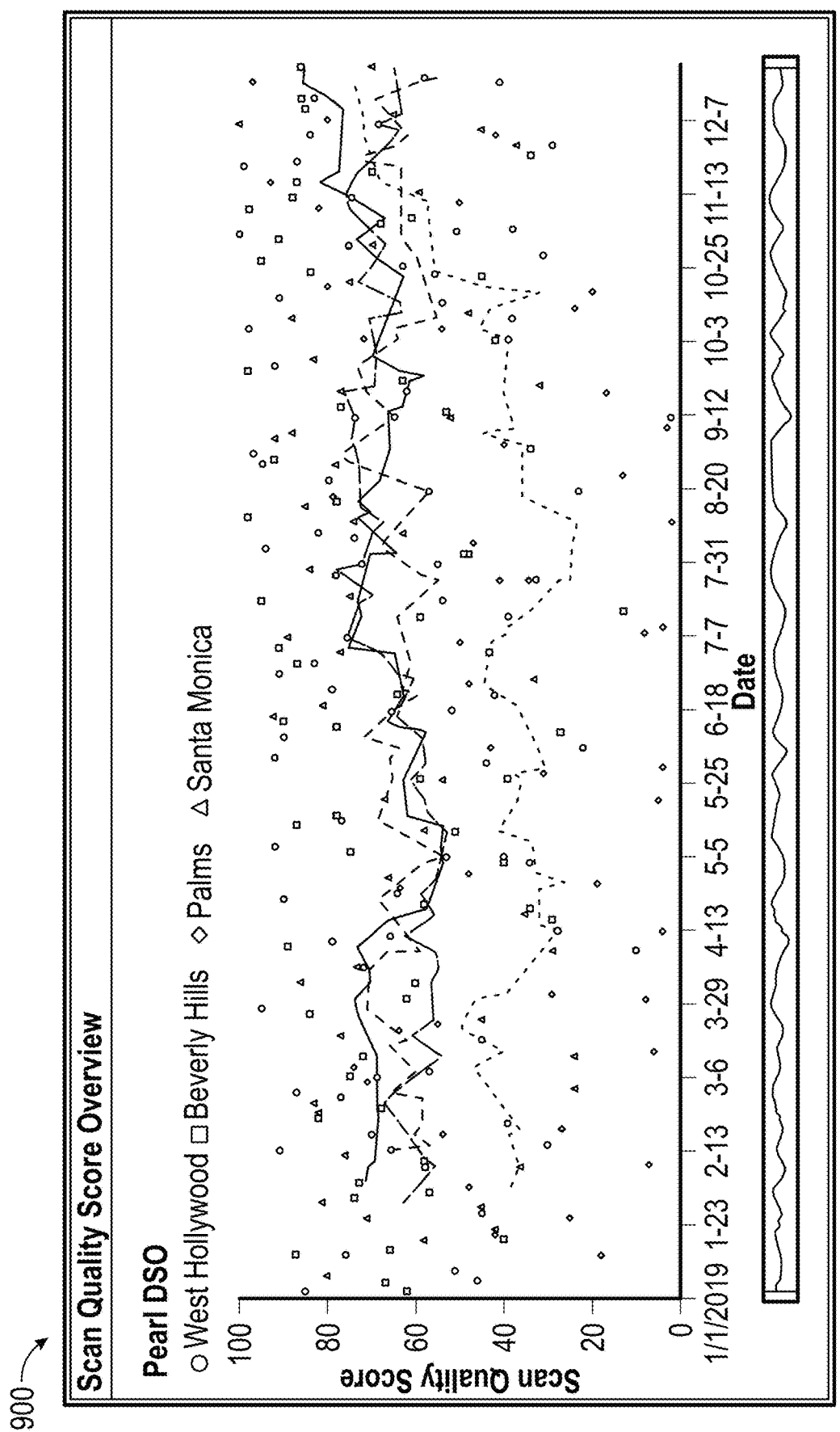
FIG. 9 depicts an illustrative user interface that presents a graph of scan quality scores determined for different office locations or dental practices.

FIG. 9 depicts an illustrative user interface 900 that presents a graph of scan quality scores determined for different office locations or dental practices. The scan quality scores may be aggregated scores of the clinicians practicing at each illustrated location (West Hollywood, Beverly Hills, etc.), where individual scores represent quality measures associated with individual intraoral scans in association with margin marking. Such scan quality scores or measures may be determined, in some embodiments, according to systems and methods described in U.S. patent application Ser. No. 16/684,427, entitled "ENHANCED TECHNIQUES FOR DETERMINATION OF DENTAL MARGINS IN INTRAORAL SCANS," filed on Nov. 14, 2019.

Figure 10:
FIG. 10 depicts an illustrative user interface that presents clinician performance data or scores for various clinicians.

FIG. 10 depicts an illustrative user interface 1000 that presents clinician performance data or scores for various clinicians. In the illustrated example, the score or percentage indicated for each dentist or other clinician for each time period (broken down into fiscal quarters) may be based on how often the clinician was determined by the system to have missed a treatment opportunity. The user interface 1000 includes options for sorting in descending or ascending score order for individual time periods, which may enable the user to quickly identify underperforming clinicians or exceptional clinicians.

FIG. 11 depicts an illustrative user interface 1100 that enables a user to define settings that include grouping offices or practices. In some embodiments, user interface 1100 may be shown to an administrative user in order to allow the user to create groups of offices, which may have associated permissions assigned. For example, one user may be authorized to view only regional office data, while another user may be able to view data across multiple geographic regions.

Figure 12:
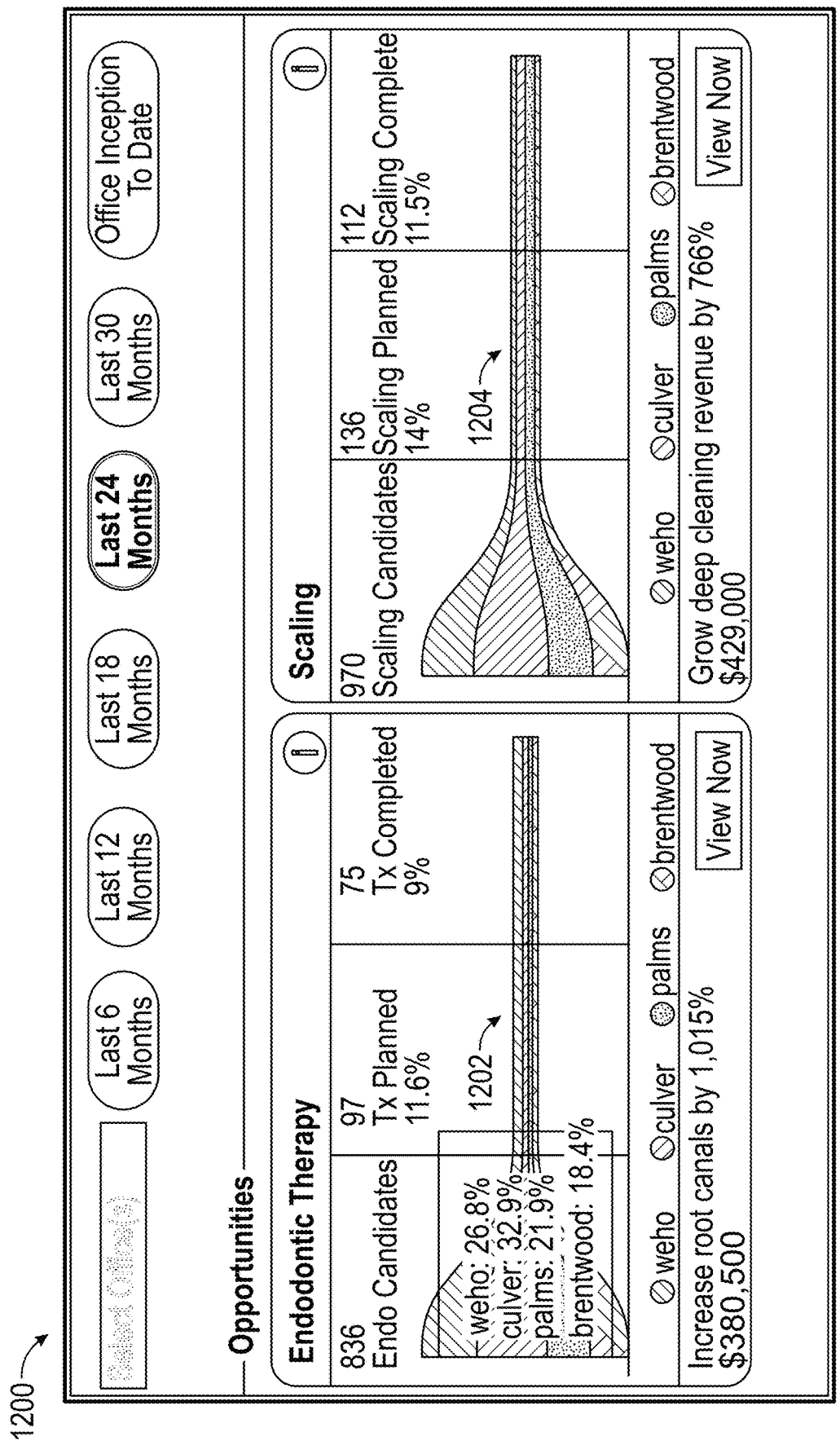
FIG. 12 depicts an illustrative user interface that presents a visual or graphical representation of the number of patient treatment opportunities in different categories as determined using machine learning.

FIG. 12 depicts an illustrative user interface 1200 that presents a visual or graphical representation of the number of patient treatment opportunities in different categories as determined using machine learning. The user interface 1200 includes a graphical funnel visualization 1202 of endodontic therapy opportunities determined by the system, and a graphical funnel visualization 1204 of scaling opportunities determined by the system. Each of the graphical funnel visualizations 1202 and 1204 is illustrated as smoothly transitioning between three states—(1) the number of candidate patients (for endodontic therapy and scaling, respectively, in this example) as determined by machine learning, (2) the subset of candidate patients for which the corresponding treatment (endodontic therapy or scaling) has been planned, and (3) the subset of candidate patients for which the treatment (endodontic therapy or scaling) has been completed.

In FIG. 12, each of graphical funnel visualizations 1202 and 1204 are broken down vertically into different offices, such as different geographic locations of dental offices within a dental practice. This allows an individual viewing the user interface 1200 to visually compare the relative performance of different offices or practices with respect to the extent to which each office plans and/or completes the treatments or procedures that the system predicts should be performed based on an automated analysis of radiographs and other patient data. The user may select to view similar funnel visualizations for other treatments or procedures, and/or across other time periods (e.g., the last 6 months, last 12 months, last 30 months, or over a specific user-defined date range).

Figure 13:
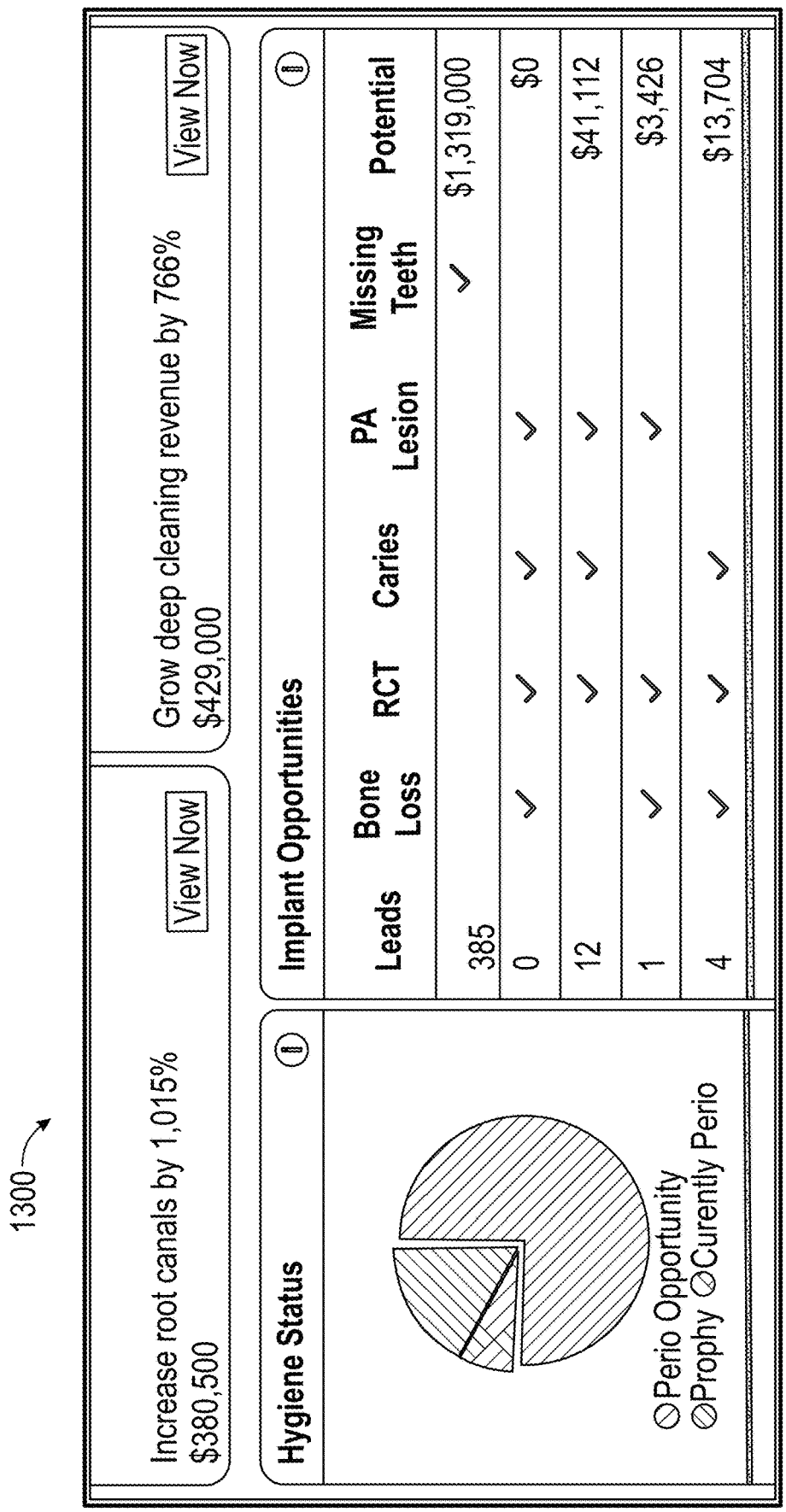
FIG. 13 depicts an illustrative user interface that presents information regarding implant opportunities as determined using machine learning, including the number of leads meeting each of various indicated combinations of conditions.

FIG. 13 depicts an illustrative user interface 1300 that presents information regarding implant opportunities as determined using machine learning, including the number of leads meeting each of various indicated combinations of conditions. Graphical element 1302, shown in this example as a pie chart, visually indicates relative amounts or percentages of the different hygiene statuses of the given patient population 13 in this case, broken down into the status categories of perio opportunity, currently perio, and prophy. The user interface 1300 further includes an implant opportunities table 1304 that indicates, for each of a number of indications (where an indication may be a combination of conditions leading to a particular treatment code), the number of patient leads that qualify for the opportunity and the potential monetary value if those implant procedures were performed (such as revenue determined by multiplying the lead count by the average per-implant revenue to the practice). As an example, the third row of table 1304 indicates that the system has identified twelve implant opportunity leads where the system determined that the respective twelve patients have signs of each of RCT, caries and PA lesion.

FIG. 14 depicts an illustrative user interface 1400 that presents a visual or graphical representation of the number of patient treatment opportunities in different categories as determined using machine learning. As illustrated, each row in the illustrated table 1402 corresponds to a different patient (listed by patient name and office name). The table includes graphical icons reading either "unscheduled" or "predicted" in certain table positions, indicating the status for the listed individuals for each of perio, endo, scaling, implant, restoration and restoration replacement. The "unscheduled" status may represent patients with at least one outstanding treatment, while the "predicted" status may represent patients where the machine learning processes found a lead but nothing has been planned for the patient. For example, the "unscheduled" entry for scaling for the patient in the first row of table 1402 indicates, in this example, that the machine learning processes identified the given patient as a candidate for a scaling procedure, but that the patient is not yet scheduled for a scaling procedure to be performed (although the patient may be scheduled for an appointment otherwise). The system may have determined, from the patient's PMS data and/or a dentist's schedule, that that no scaling procedure has been planned or scheduled for the patient despite the system identifying (based on radiographs and other data as of Mar. 4, 2020, as indicated by the "AI Date" entry in the table, for example) that there is a scaling opportunity for that patient.

The user may select to sort or filter the rows in table 1402 in various ways, such as by treatment status, last appointment, opportunity type, etc. Accordingly, the user interface 1400 may generally enable a user involved in practice management to build a list of leads that are most outstanding and/or severe. The user may choose, for example, to filter by "unscheduled" status to prioritize patients who are not yet scheduled for a treatment that the system has identified appears to be appropriate for the patient. User selection of the "more filters" option 1404 may cause presentation of a user interface or pop-up window similar to that shown in FIG. 15. FIG. 15 depicts an illustrative user interface 1500 that provides options to a user for filtering patient information such as that shown in FIG. 14. The user may select one or more of the checkboxes displayed in user interface 1500 and/or modify the time period range during which the corresponding AI or machine learning-based detections were made in order to filter a subsequently displayed list of patient opportunities.

Figure 16:
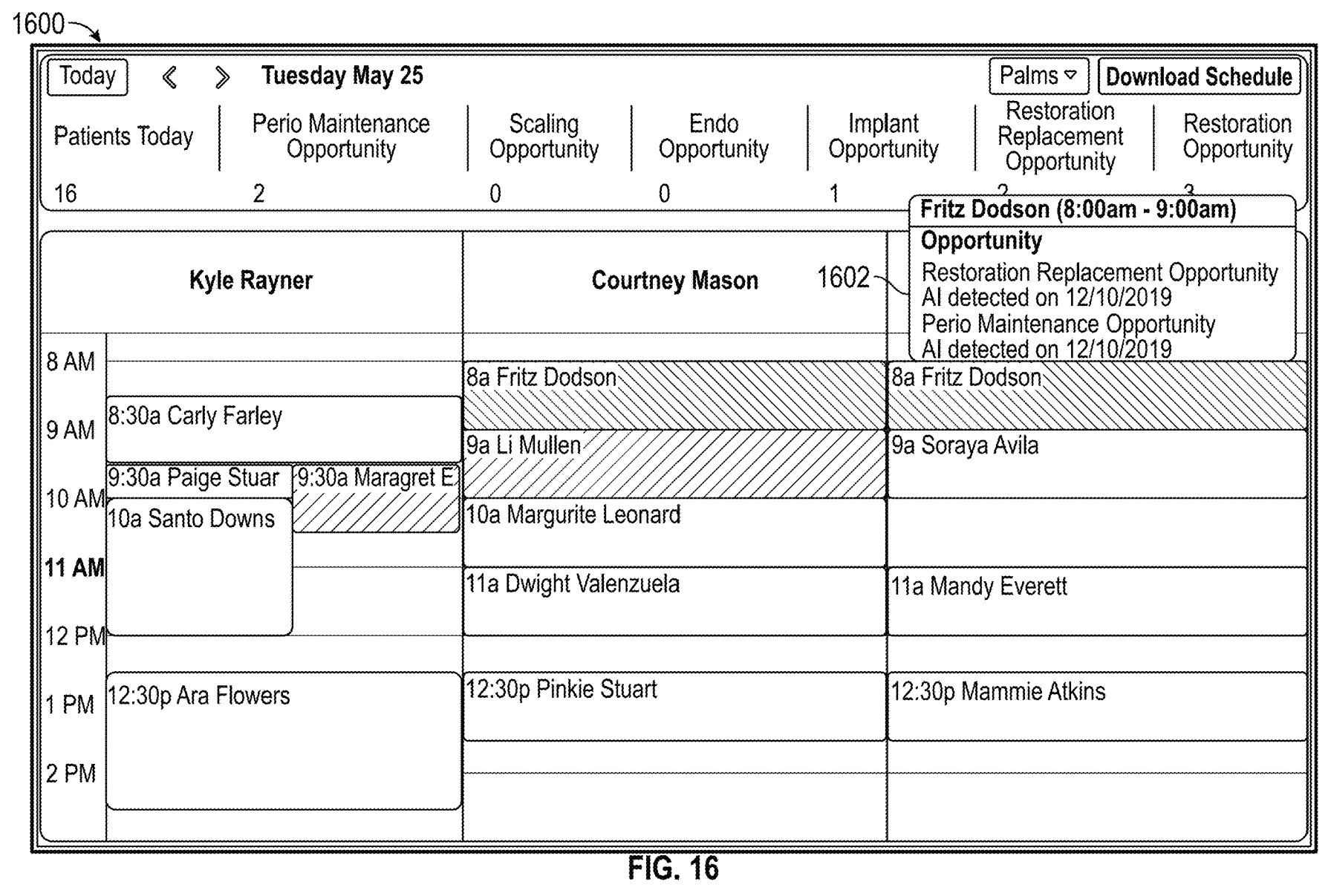

FIG. 16 depicts an illustrative user interface 1600 providing an overview of a schedule for a given day for a dental office or dental practice. The user interface 1600 indicates, for the sixteen patients scheduled for that day, the number of treatment opportunities (broken down by number of perio maintenance opportunities, scaling opportunities, endo opportunities, implant opportunities, restoration replacement opportunities, and restoration opportunities) as determined by the system using machine learning. While aspects of the presented schedule may be similar to scheduling displays that have traditionally been presented to doctors in past systems (such as during a "morning huddle" before the office day begins), past scheduling displays may be limited to presenting PMS data, doctor notes, past visit cadence, etc., rather than the machine learning-based automated determinations that drive aspects of the generated user interface 1600. For example, pop-up display 1602 (which may be displayed upon a mouseover or touch event with respect to a particular patient's schedule entry) indicates that a patient scheduled for a 8:00 am appointment that day is the subject of two opportunities that have been automatically determined by the machine learning processes described herein—in this case, a restoration replacement opportunity (detected by AI or machine learning on Dec. 10, 2019) and a perio maintenance opportunity (also detected by AI or machine learning on Dec. 10, 2019).

Figure 17:
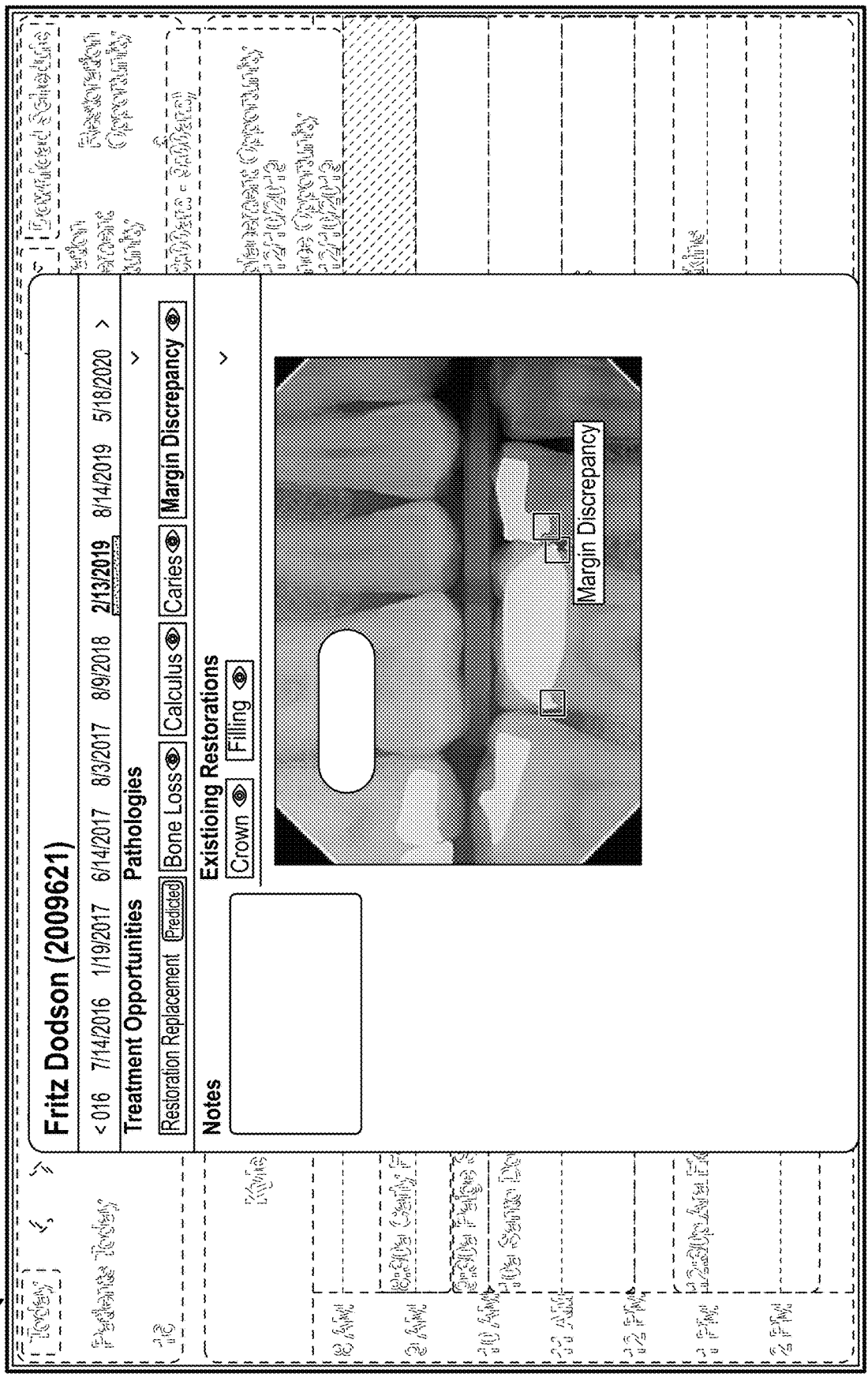
FIGS. 17 and 18 depict illustrative user interfaces that provide a detailed view of patient data, each for a different individual patient.
Figure 18:
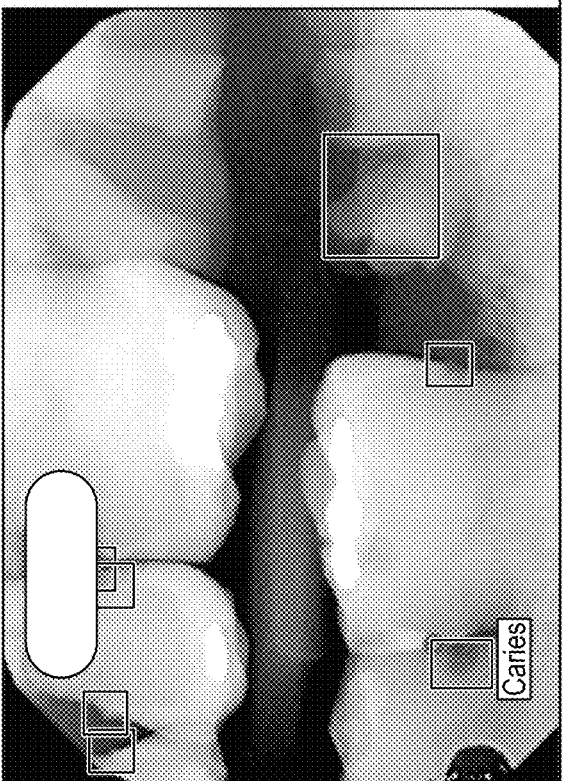

FIGS. 17 and 18 depict illustrative user interfaces 1700 and 1800 that provide a detailed view of patient data, each for a different individual patient. The user interfaces 1700 and 1800 identify, for example, treatment opportunities discovered by the machine learning models for the respective patient (including unscheduled and predicted treatments), pathologies and existing restorations. The user interfaces 1700 and 1800 each include a radiograph for the respective patients on which bounding boxes are overlaid to identify locations of selected pathologies and/or existing restorations (as determined by the machine learning models). The user may toggle on or off which pathologies are displayed with bounding boxes, and may additionally add associated notes (such as a doctor noting to discuss a particular opportunity with the patient). A doctor may view such a user interface for purposes of internal review or planning, or may show the marked radiograph to a patient when explaining support or reasoning for recommending a treatment. A user interface similar to user interfaces 1700 or 1800 may provide an option for a doctor to print a marked copy of the radiograph (e.g., with bounding boxes and associated labels marked, as shown) for presentation to the patient. In some embodiments, such a user interface may include an option for a doctor to dismiss one or more of the opportunities and/or pathologies (such as if the doctor disagrees with output of the machine learning models).

Figure 19:
FIG. 19 depicts a digital "call sheet" user interface that organizes treatment leads based on criteria that may be set by a user, such as a doctor, an office administrator or practice management personnel.
Figure 20:
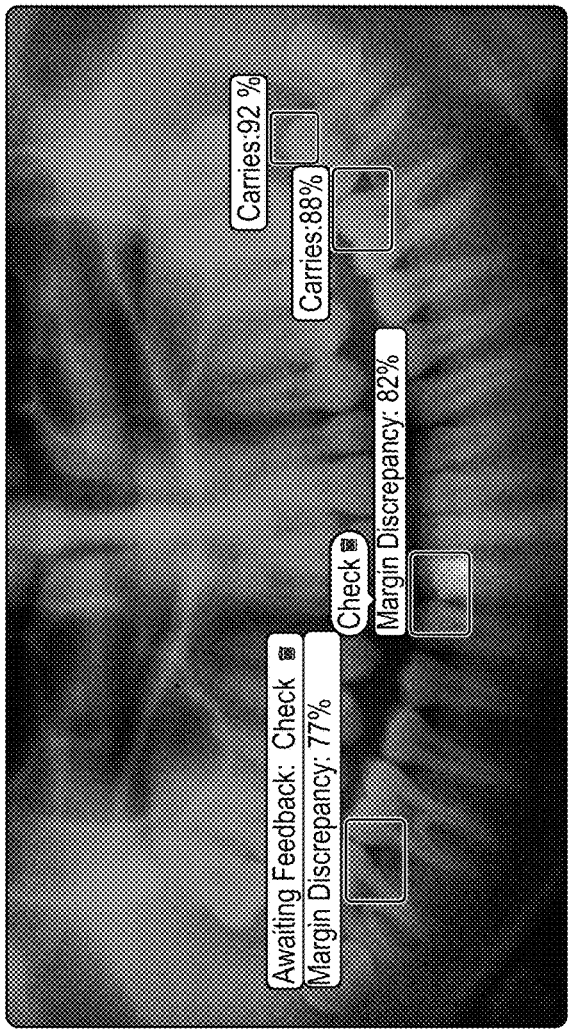
FIG. 20 depicts an illustrative user interface that includes AI-detected pathologies for a particular patient shown as overlaid information and associated bounding boxes on a radiograph of the patient.

FIG. 19 depicts a digital "call sheet" user interface 1900 that organizes treatment leads based on criteria that may be set by a user, such as a doctor, an office administrator or practice management personnel. For example, in the illustrated example, a doctor may have set up various automated lists including "recall due" (set with criteria for the system to identify patients ready or overdue for recall), "recall due and unscheduled treatment plan" (set with criteria for the system to identify patients ready or overdue for recall with planned yet outstanding treatments), "recall due and AI predicted opportunities" (set with criteria for the system to identify patients ready or overdue for recall with potential unmet treatment needs predicted by AI or machine learning), etc. Each card or UI section displayed on the digital call sheet user interface 1900 indicates the applicable time range, number of patient matches, and potential dollar amount of the opportunities. A user may select a card or UI section to see additional information, such as patient details, as well as to initiate contact with a listed patient (such as by initiating a phone call, sending an email, or sending a text message) or to schedule a listed patient for a treatment.

Additional Features

In some embodiments, the computing system 802 may check that conditions, treatments or other issues identified or predicted by machine learning models in the past for particular patients have later been resolved by a later-performed treatment or otherwise. For example, the system may have determined last year that a particular patient has signs of calculus in a radiograph, and may then later check whether that calculus has been resolved based on machine learning analysis of the same tooth in a subsequently captured radiograph from a later patient visit. The system may assign a unique identifier to a particular finding of the machine learning models for a particular patient and date, and may then track changes to that finding in subsequent radiographs. Output of such a process may include, for example, the system identifying that a particular margin discrepancy was first identified for a given patient in a September 2016 intraoral scan, was still not addressed as of an August 2018 scan, but was then addressed (as determined from an updated intraoral scan, radiograph and/or PMS data regarding a patient appointment) in March 2019. In some instances, tooth decay or other conditions identified by the system may have been raised with a patient when the conditions were not severe, which the patient may have selected to ignore initially, but the system may then track worsening of the condition during subsequent patient visits (e.g., the system may present a message that the machine learning models identified 30% worse tooth decay between successive patient visits), resulting in the patient and doctor ultimately deciding to treat the condition.

In some embodiments, the computing system 802 may provide an option for a doctor to request that the system automatically fill available times on the doctor's calendar with patients based on the machine learning models' identification of treatment opportunities (pending patient acceptance of the recommendation and patient availability). For example, a user may, on behalf of a given doctor or office, specify logic (such as targeting specific conditions based on severity) that the system should employ in filling space on a doctor's calendar as stored within a PMS database. In some embodiments, a practice administrator or manager may indicate that a particular doctor may want to consider better identifying bone loss based on the results of the machine learning processes, and the doctor may then request that the system identify the strongest candidates for bone loss treatment and/or automatically schedule the top x patients meeting the desired criteria of the doctor.

Figure 21:
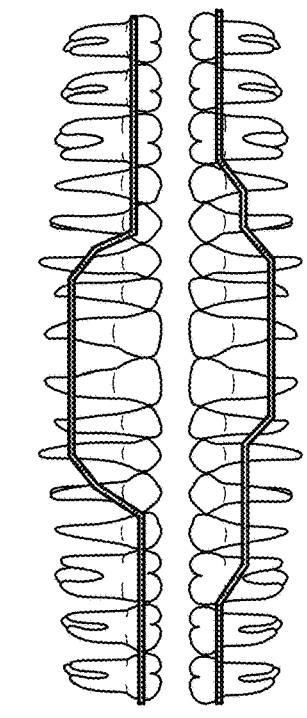

In some embodiments, the medical image analysis system 120 and/or data distribution and management system 140 may write data to a PMS system or database. For example, in addition to modifying or adding entries to a doctor's calendar in a PMS data store, as described above, one or more systems described above may add data to a patient's chart data in a PMS data store, such as predicted or detected pocket depth (or probe depth) information as determined from radiograph analysis by machine learning models, among other predictions or determinations of the above-discussed machine learning models. For example, while a patient's tissue does not show on an X-ray, machine learning techniques may be applied to an X-ray to predict and measure the distance between, on each tooth, the top of bone (e.g., bone crest) to the top of the tooth (e.g., the cemento-enamel junction (CEJ)), which the system may then map to a probing depth for each tooth and generate a chart with each tooth's predicted probing depth, which may be graphically presented in perio-related portions of a user interface such as those shown in portion 2102 of user interface 2100 in FIG. 21 or in portion 2202 (which may be displayed as a color gradient, such as from green representing acceptable depth to yellow to red, indicating progressively worsening probing depth predictions, in some embodiments) of user interface 2200 of FIG. 22. As another example, the system may generate treatment plans automatically for a patient, which are then added by the system to the PMS data for that patient. For example, if a particular patient needs an implant, the system may suggest treatment details such as insertion angle, material, etc., as well as how parts of the procedure should be split between different visits to the doctor by the patient.

As another example, the system may certify leads or treatments as approved by the automated methods described herein, and may store an indication in the PMS data that a treatment for a particular patient is approved or certified by an entity operating or associated with the medical image analysis system 120. In some embodiments, the system may certify a lead or treatment when the machine learning models' confidence score is above a predetermined confidence threshold that the underlying condition(s) or indication(s) are present. In some embodiments, a seal, watermark or other visual indication of certification may be added automatically by the system to the patient's radiographs or other documents analyzed by the system, which the system may provide to the patient, another doctor (e.g., in association with a doctor referral), an insurance company, or other third party. For example, a certification seal or certification metadata accompanying a radiograph or patient record may indicate the date that the radiograph(s) were analyzed by the system and approved, which may signify to an insurance company that no further investigation is needed to process an insurance claim in view of the certification. In some embodiments, the certification may also represent that the system did not detect evidence of fraud, waste or abuse, as discussed in more detail in U.S. patent application Ser. No. 17/075,607, entitled "COMPUTER VISION-BASED CLAIMS PROCESSING," referenced above.

In some embodiments, the system may determine and apply certifications at the practice or office level, rather than or in addition to certifying radiographs for a particular patient. For example, the system may analyze treatments performed by a given dental office or practice over a certain time period (e.g., quarterly, annually, etc.) to determine if any under-treatment or overtreatment (based on the machine learning models' analysis) is in an acceptable range for certification by the system. An operator of the system may allow certified practices to advertise their certification status (such as providing an associated sticker or certificate for display in the doctor's office) and/or may provide the certification status to an insurer for fast-tracking insurance claims from the given office.

In some embodiments, similar methods that may be employed to certify a practice may be used in other contexts, such as in due diligence when a practice is being acquired or for practice audits. For example, if a DSO is interested in purchasing a medical practice, systems and methods described herein may provide a more holistic and detailed analysis of the quality of the practice from a dental or medical perspective compared to existing techniques (such as manually reviewing records for a small randomly selected group of the practice's patients). These automated review techniques may provide a number of benefits, including helping an acquiring DSO to identify whether they may be inheriting liability for overtreatment or other care issues. The system may output, for example, the practice's statistics described elsewhere herein, as well as a ranked list of the most likely instances of overtreatment or under-treatment for human review.

Additional user interfaces other than those of the types mentioned above and shown in the figures may be provided, in some embodiments. For example, a user interface may be presented that enables a DSO or other user managing one or more practices to see whether any offices or specific clinicians being managed by the user have had insurance claims flagged as potentially fraudulent by the system or a related system. For example, machine learning techniques may be employed to analyze insurance claim data and associated supporting documentation (such as radiographs) to determine whether the insurance claim may be fraudulent based on determinations such as whether image signatures generated for the supporting images match image signatures from prior submitted claims for different patients (indicating that a provider may be submitting a radiograph of a different patient to support a procedure being necessary). Systems and methods for performing such analysis of insurance claims are described in U.S. patent application Ser. No. 17/075,607, entitled "COMPUTER VISION-BASED CLAIMS PROCESSING," filed Oct. 20, 2020, which is hereby incorporated by reference herein.

It will be appreciated that the various different funnels, processes and methods described herein above regarding combined analysis of PMS data and detected indications or other features in radiographs (such as one or more pathologies) may be used in a variety of specific use cases. As one example, pathologies and/or image features indicative of the need for orthodontic intervention may be coupled with a patient's orthodontic status as indicated in PMS data. These detected pathologies/features indicative of the need for orthodontic intervention may include at least one of but aren't limited to: tooth crowding, anticipated crowding, root parallelism, improper tooth spacing, improper root lengths, impactions, mesial tilting, missing teeth, interproximal contact overlapping, and/or mandibular asymmetry. As a second example, detection of furcation by the machine learning models may be reviewed by the system with respect to a planned or unplanned extraction or implant surgery as indicated in PMS data. As a third example use case, detection of poor image quality by the machine learning models may indicate the need for new radiographs to be taken (which may be indicated to a doctor or practice manager via a user interface). As a fourth example, detection of caries/decay by the machine learning models may be reviewed by the system with respect to a planned or unplanned crown, filling, and/or inlay treatment as indicated in the PMS data. As another example, detection of a margin discrepancy by the machine learning models may be reviewed by the system with respect to planned or unplanned crown treatment in the PMS data. As another example, detection of a margin discrepancy in post-op imagery may be used to perform or assess quality control regarding a recently installed dental restoration. As a further example, detection of impacted teeth by the machine learning models may be reviewed by the system with respect to planned or unplanned extractions, exposure and/or brackets.

The various different funnels, processes and methods described herein above regarding combined analysis of PMS data and detected indications in radiographs (such as one or more pathologies) can be used to determine both overtreatment and under treatment by a practitioner. As an example with respect to under treatment, machine learning models may detect an indication in a radiograph but the corresponding PMS data may not contain an associated treatment code (for example, the doctor didn't find a patient to have bone loss but the machine learning models detected bone loss). Alternatively, as an example with respect to overtreatment, machine learning models may not detect a particular indication in radiographs when the PMS data does contain an associated treatment code (for example, the doctor said that a patient has bone loss but the machine learning models do not detect bone loss in the patient's radiographs). Overtreatment may be detected in cases where there is no fraud or fraudulent intent by a doctor—for example, the doctor may simply be applying a different standard than the machine learning models regarding when the doctor believes treatment is needed or would be beneficial to a patient.

In some embodiments, aspects of the present disclosure may include enabling a user, such as a doctor, to define a funnel or rule set for mapping certain outputs or classifications made by the machine learning models to particular treatments. For example, a doctor may define a custom funnel indicating that five or more instance of calculus (as predicted by machine learning models) on different teeth of a patient should be flagged or identified by the system as an opportunity for scaling. An individual doctor could define any number of custom criteria that the system should map to certain treatment opportunities for patients of that particular doctor going forward. In some instances, the rules may take a form similar to that described from the insurance carrier's side in U.S. patent application Ser. No. 17/075,607 (incorporated by reference above), such as with respect to FIG. 14 of that application, with the result of individual rules leading to a specified treatment recommendation.

In some instances, the system may write directly to PMS data when conditions are detected or treatments are recommended based on defined criteria. For example, if a rule has been set for a particular doctor or practice indicating that bone loss greater than 0.5 should lead to a certain treatment (which may be a rule defined within the PMS, in some embodiments), an instance of such a finding may result in the system storing in the PMS data for the patient that the given treatment should be performed during the patient's next visit. In some embodiments, the system may first check with the doctor, such as presenting a message in a user interface asking the doctor whether the doctor agrees with the automated determination (e.g., displaying a marked radiograph with a question such as "Do you agree that this patient needs a filling?" along with selectable options for the doctor to indicate agreement or disagreement).

In some embodiments, the methods and systems described herein may be used in connection with a blind referral service for doctors, such as a bi-directional referral service provided between general practitioners and specialists. For example, a doctor may refer their patient to an oral surgeon, who may then be granted access within the system to marked radiographs (as described herein, with indications or conditions marked using machine learning). Through the system, the oral surgeon may indicate that he or she would like to see the patient. The communication channel between doctors may be secure and may also be anonymized with respect to the identity of the patient and optionally the referring doctor.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more general purpose computers or processors. The code modules may be stored in any type of non-transitory computer-readable medium or other computer storage device. Some or all the methods may alternatively be embodied in specialized computer hardware. In addition, the components referred to herein may be implemented in hardware, software, firmware or a combination thereof.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

It should be emphasized that many variations and modifications may be made to the above-described embodiments, the elements of which are to be understood as being among other acceptable examples. All such modifications and variations are intended to be included herein within the scope of this disclosure.

What is claimed is:

1. A computer system comprising:
   one or more electronic data stores that store data mapping each of a plurality of dental conditions to a corresponding dental treatment; and
   a processor in communication with the one or more electronic data stores and configured with processor-executable instructions to perform operations comprising:
   training, using a plurality of training images depicting dental radiographs as training image data, a plurality of machine learning models to localize and classify dental conditions depicted in the training image data, wherein at least a subset of the plurality of machine learning models comprise neural networks;
   obtaining patient records originating from a practice management system of a dental provider, wherein the patient records include, for each patient of a plurality of patients, at least one of (a) an indication of whether the patient has been classified by a dental provider as prophylaxis (prophy) or periodontal (perio), or (b) a treatment code identifying a dental treatment performed on the patient by the dental provider;
   providing, for each of the plurality of patients, at least one radiograph of the patient as input to one or more trained machine learning models of the plurality of machine learning models;
   receiving, for each of the plurality of patients, output of the one or more machine learning models that are provided with the input comprising the at least one radiograph of the patient, wherein the output of the one or more machine learning models identifies at least one dental condition determined by the one or more machine learning models to be depicted in the at least one radiograph of the patient;
   analyzing conditions identified in radiographs by the one or more machine learning models with respect to treatments identified in corresponding patient records from the practice management system;
   based at least in part on instances in which a condition identified by the one or more machine learning models does not match corresponding data from records in the practice management system, identifying a plurality of missed periodontal opportunities associated with the dental provider, wherein the instances are identified based at least in part on the data mapping each of the plurality of dental conditions to the corresponding dental treatment;
   generating provider performance data regarding the dental provider for a time period, wherein the provider performance data comprises a numeric score or percentage representing how often, based on the instances in which the condition identified by the one or more machine learning models does not match the corresponding data from records in the practice management system, the dental provider missed periodontal opportunities among a plurality of patients that visited the dental provider over the time period; and generating a user interface that presents at least the provider performance data regarding the dental provider over the time period.

2. The computer system of claim 1, wherein the user interface further presents information regarding each of at least a subset of the plurality of periodontal opportunities missed by the dental provider during prior patient visits as determined based on output of the one or more machine learning models.

3. The computer system of claim 1, wherein the one or more machine learning models further comprise machine learning models that utilize deep learning to (1) localize one or more regions in the radiograph which contain features of interest and (2) classify each of the one or more regions as depicting one or more pathologies, restorations, anatomies, or anomalies.

4. The computer system of claim 1, wherein one of the instances in which the condition identified by the one or more machine learning models does not match corresponding data from the records in the practice management system comprises an instance in which a first treatment code expected for a first patient based on a first corresponding condition being identified in a first radiograph by the one or more machine learning models does not appear in practice management system records for the first patient.

5. The computer system of claim 1, wherein one of the instances in which the condition identified by the one or more machine learning models does not match corresponding data from the records in the practice management system comprises an instance in which a first patient classified as periodontal by the one or more machine learning models is indicated as prophylaxis in the PMS data.

6. The computer system of claim 1, wherein the user interface further identifies a plurality of treatment leads based on output of the one or more machine learning models and criteria set by a user associated with the dental provider.

7. The computer system of claim 6, wherein the criteria set by the user comprises doctor-specific weights to be applied by the computer system to each of a plurality of different conditions or indications that the one or more machine learning models are trained to detect in radiographs.

8. The computer system of claim 1, wherein the user interface further presents a graphical funnel visualization that includes a visual transitions between three states—(1) a representation of a number of candidate patients for a dental procedure as determined by the one or more machine learning models, (2) a first subset of candidate patients for which the dental procedure has been planned, and (3) a second subset of candidate patients for which the dental procedure has been completed.

9. A computer-implemented method comprising:
as implemented by one or more computing devices configured with specific executable instructions,
training, using a plurality of training images depicting dental radiographs as training image data, a plurality of machine learning models to localize and classify dental conditions depicted in the training image data, wherein at least a subset of the plurality of machine learning models comprise neural networks;
obtaining, for a plurality of patients of a dental provider, patient records originating from a practice management system of the dental provider;
providing, for each of the plurality of patients, at least one radiograph of the patient as input to one or more trained machine learning models of the plurality of machine learning models;
receiving, for each of the plurality of patients, output of the one or more machine learning models that are provided with the input comprising the at least one radiograph of the patient, wherein the output of the one or more machine learning models identifies at least one dental condition determined by the one or more machine learning models to be depicted in the at least one radiograph of the patient;
comparing conditions identified in radiographs by the one or more machine learning models with treatments identified in corresponding patient records from the practice management system;
based at least in part on instances in which a condition identified by the one or more machine learning models does not match corresponding data from records in the practice management system, identifying a plurality of missed periodontal opportunities associated with the dental provider, wherein the instances are identified based at least in part on data mapping each of a plurality of dental conditions to a corresponding dental treatment;
generating provider performance data regarding the dental provider for a time period, wherein the provider performance data comprises a numeric score or percentage representing how often, based on the instances in which the condition identified by the one or more machine learning models does not match the corresponding data from records in the practice management system, the dental provider missed periodontal opportunities among a plurality of patients that visited the dental provider over the time period; and
generating a user interface that presents at least the provider performance data regarding the dental provider over the time period.

10. The computer-implemented method of claim 9, further comprising identifying a first patient with potential unmet dental treatment needs based on a comparison of output of the one or more machine learning models with information from a patient record of the first patient.

11. The computer-implemented method of claim 10, further comprising generating, for display in a second user interface, an overview of one or more predicted dental treatments for the first patient based on output of the machine learning models when provided with one or more radiographs of the first patient as input.

12. The computer-implemented method of claim 10, further comprising generating, for display in a second user interface, a graphical depiction of estimated probe depth information for each of a plurality of teeth of the first patient as determined via machine learning analysis of a radiograph of the first patient.

13. The computer-implemented method of claim 9, wherein the user interface further includes information identifying a plurality of dental implant opportunities as determined using the one or more machine learning models, wherein the information includes indication of a number of patients meeting each of a selected combination of dental conditions.

14. The computer-implemented method of claim 9, wherein the user interface further includes a determined estimated revenue that could be obtained by the dental provider as a result of a set of patients identified by the one or more machine learning models as incorrectly prophylaxis were instead moved to periodontal status.

15. A computer-readable, non-transitory storage medium storing computer executable instructions that, when executed by one or more computer systems, configure the one or more computer systems to perform operations comprising:

training, using a plurality of training images depicting dental radiographs as training image data, a plurality of machine learning models to localize and classify dental conditions depicted in the training image data, wherein at least a subset of the plurality of machine learning models comprise neural networks;

obtaining, for a plurality of patients of a dental provider, patient records originating from a practice management system of the dental provider;

providing, for each of the plurality of patients, at least one radiograph of the patient as input to one or more trained machine learning models of the plurality of machine learning models;

receiving, for each of the plurality of patients, output of the one or more machine learning models that are provided with the input comprising the at least one radiograph of the patient, wherein the output of the one or more machine learning models identifies at least one dental condition determined by the one or more machine learning models to be depicted in the at least one radiograph of the patient;

comparing conditions identified in radiographs by the one or more machine learning models with treatments identified in corresponding patient records from the practice management system;

based at least in part on instances in which a condition identified by the one or more machine learning models does not match corresponding data from records in the practice management system, identifying a plurality of missed periodontal opportunities associated with the dental provider, wherein the instances are identified based at least in part on data mapping each of a plurality of dental conditions to a corresponding dental treatment;

generating provider performance data regarding the dental provider for a time period, wherein the provider performance data comprises a numeric score or percentage representing how often, based on the instances in which the condition identified by the one or more machine learning models does not match the corresponding data from records in the practice management system, the dental provider missed periodontal opportunities among a plurality of patients that visited the dental provider over the time period; and generating a user interface that presents the provider performance data regarding the dental provider over the time period.

* * * * *